Figure 1:
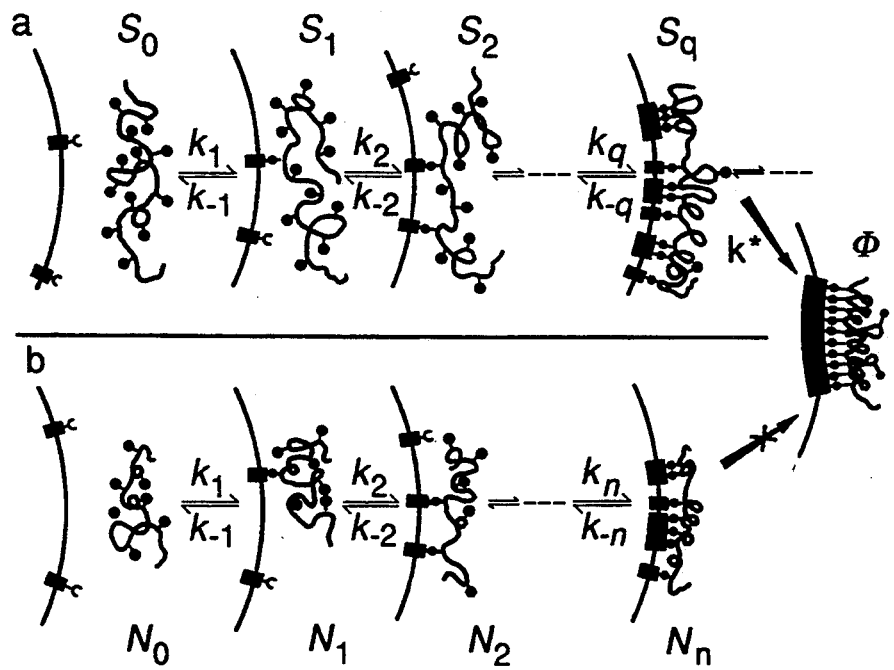

US005370871A

United States Patent [19]
Dintzis et al.

[11] Patent Number: 5,370,871
[45] Date of Patent: Dec. 6, 1994

[54] THERAPEUTIC SUPPRESSION OF SPECIFIC IMMUNE RESPONSES BY ADMINISTRATION OF OLIGOMERIC FORMS OF ANTIGEN OF CONTROLLED CHEMISTRY

[75] Inventors: Howard M. Dintzis; Renee Z. Dintzis, both of Baltimore, Md.

[73] Assignee: The Johns Hopkins University, Baltimore, Md.

[21] Appl. No.: 49,601

[22] Filed: Apr. 20, 1993

Related U.S. Application Data

[63] Continuation of Ser. No. 354,710, May 22, 1989, which is a continuation-in-part of Ser. No. 248,293, Sep. 21, 1988, Pat. No. 5,126,121, which is a continuation of Ser. No. 869,808, May 29, 1986, abandoned, which is a continuation of Ser. No. 460,266, Jan. 24, 1983, abandoned.

[51] Int. Cl.[5] .................. A61K 39/00; A61K 39/116; A61K 39/385
[52] U.S. Cl. ................ 424/244.1; 424/184.1; 514/2; 514/23; 514/25; 530/412; 530/417; 530/807; 536/123.1
[58] Field of Search ............... 530/402, 403, 412, 413, 530/807, 868, 417; 424/88, 92; 514/2, 23, 25; 536/123.1

[56] References Cited

U.S. PATENT DOCUMENTS

| | | | |
|---|---|---|---|
| 3,794,630 | 2/1974 | Mullan | 260/112 R |
| 3,869,546 | 3/1975 | Lund | 424/88 |
| 3,919,411 | 11/1975 | Glass | 424/81 |
| 4,123,520 | 10/1978 | Hagopian et al. | 424/92 |
| 4,140,679 | 2/1979 | Malley | 260/857 R |
| 4,164,565 | 8/1979 | Prince et al. | 424/89 |
| 4,191,668 | 3/1980 | Katz | 260/6 |
| 4,220,565 | 9/1980 | Katz | 260/6 |
| 4,222,907 | 9/1980 | Katz | 260/6 |
| 4,242,501 | 12/1980 | Cano et al. | 536/1 |
| 4,253,995 | 3/1981 | Katz | 260/6 |
| 4,253,996 | 3/1981 | Katz | 260/6 |
| 4,261,973 | 4/1981 | Lee | 424/78 |
| 4,276,206 | 6/1981 | Katz | 260/6 |
| 4,296,097 | 10/1981 | Lee | 424/78 |
| 4,310,514 | 1/1982 | Durette | 424/88 |
| 4,388,441 | 6/1983 | Katz | 525/54.1 |
| 4,430,260 | 2/1984 | Lee | 260/239.1 |
| 4,496,654 | 1/1985 | Katz | 435/7 |
| 4,673,574 | 6/1987 | Anderson et al. | 424/92 |
| 4,874,794 | 10/1989 | Katz | 514/724 |
| 5,126,131 | 6/1992 | Dintzis | 424/88 |

OTHER PUBLICATIONS

Dintzis, R. Z., et al., PNAS (USA) 79:884–888 (Feb., 1982), "Specific cellular stimulation in the primary immune response: experimental test of a quantized model".
Liu-PNAS 76:1430–1434 (1979).
Feldman, Extracellular Matrix Influences on Gene Expression, p. 467.
Feldman, M., J. of Exp. Med 135:735–752 (1972), "Induction of immunity and tolerance in vitro by hapten protein conjugates".
Brown, Acta Allergologica 31:22 (1976).
Dintzis, H. M., et al., PNAS (USA) 73(10):3671–3675 (Oct., 1976), "Molecular determinants of immunogenicity: the immunon model of immune response".

(List continued on next page.)

*Primary Examiner*—Christine M. Nucker
*Assistant Examiner*—Thomas M. Cunningham
*Attorney, Agent, or Firm*—Cushman, Darby & Cushman

[57] ABSTRACT

The present invention relates to a vaccine derived from a bacterial or virus product that initially comprises a mixture of polymers of varying molecular weights. The vaccine contains an immunogenically effective polymer comprising T-cell-independent antigen as the effective immunizing agent. The vaccine is free of low molecular weight immunosuppressive antigen-containing polymer as a result of processing of the bacterial or virus product mixture.

4 Claims, 9 Drawing Sheets

OTHER PUBLICATIONS

Chiorazzi, PNAS 73-2091 (1976).

Dintzis, R. Z., et al., J. Immunology 131(5):2196-2203 (Nov., 1983), "Studies on the immunogenicity and tolerogenicity of T-independent antigens".

R. Scopes, *Protein Purification* (1982), pp. 151-162, Springer-Verlag.

Dintzis, H. M., et al., Theoretical Immunology, part 1:83-102 (1988), "A molecular basis for immune regulation: the immunon hypothesis".

Dintzis, H. M., et al., Immunological Reviews 115:243-251 (1990), "Antigens as immunoregulators".

Dintzis, H. M., et al., P.N.A.S. (USA) 89:1113-1117 (Feb., 1992), "Profound specific suppression by antigen of persistent IgM, IgG, and IgE antibody production".

Dintzis, R. Z., et al., P.N.A.S. (USA) 135(1):423-427 (Jul., 1985), "Inhibition of anti-DNP antibody formation by high doses of DNP-polyacrylamide molecules; effects of hapten density and hapten valence".

Dintzis, R. Z. et al., J. Immunol. 143:1239-1244 (Aug. 15, 1989), "The immunogenicity of soluble haptenated polymers is determined by molecular mass and hapten valence".

Dintzis, R. Z., et al., Eur. J. Immunology 20:229-232 (1990), "Inhibition of antibody formation by receptor cross-linking: the molecular characteristics of inhibitory haptenated polymers".

Porro, M., et al., J. Biological Standardization 11:65-74 (1983), "Immunoelectrophoretic characterization of the molecular weight polydispersion of polysaccharides in multivalent bacterial capsular vaccines".

THERAPEUTIC SUPPRESSION OF SPECIFIC IMMUNE RESPONSES BY ADMINISTRATION OF OLIGOMERIC FORMS OF ANTIGEN OF CONTROLLED CHEMISTRY

The invention described herein was made in the course of work under a grant or award from the Department of Health and Human Services and a grant by the U.S. Army Medical Research and Development Command, Contract DAMD 17-86-C-6038.

The present application is a continuation of Ser. No. 354,710, filed May 22, 1989, which is continuation-in-part of Ser. No. 07/248,293, filed Sep. 21, 1988, now U.S. Pat. No. 5,126,121, a continuation of Ser. No. 06/869,808 filed May 29, 1986, now abandoned a continuation of Ser. No. 460,266, filed Jan. 24, 1983 now abandoned.

The present invention is concerned with the therapeutic suspension of undesired immune responses. The invention is also concerned with the provision of vaccines of improved effectiveness.

It is well known that the immune systems of living animals synthesize antibodies in response to the presence of a foreign substances or organisms (i.e., an antigen) in the body. These antibodies have a specific affinity for the foreign substance which causes the antibodies to be synthesized. It is understood that such synthesis is triggered by the binding of the antigen to the receptors for the antigen on, or extending from, the surface of B-lymphocytes. This contact causes the specific cells involved to begin dividing, and creating antibodies which, under normal circumstances, defend the animal body against the specific antigen which triggered the antibody formation.

There are, however, certain situations where the body produces an immune response which is undesirable. Such responses include, for example, allergic reactions which are characterized by the production of IgE antibodies to extrinsic antigens, and autoimmune diseases where antibodies are produced against self-antigens so that, in a sense, the immune system is working against the body rather than in support of it. Organ transplants, such as a replacement kidney or liver, present other specific situations of undesired immune response where the transplant may be rejected by the body by the generation of antibodies which, in essence, attack the transplant as foreign to the body.

In the past, allergic conditions have generally been treated by repeated small stimulatory doses of antigen which are administered in the expectation that high resulting levels of specific antibody of type IgG will attenuate the deleterious effects of specific antibodies of the class IgE. Disadvantages of this treatment protocol include the danger of anaphylactic reaction to the stimulatory doses used and the inconvenience and discomfort caused by frequent injections and increasing doses of allergen causing localized pain, erythema and swelling.

The treatment of autoimmune diseases, e.g. multiple sclerosis or myasthenia gravis, varies with the type of autoimmune disease. However, such treatments which exist do not in general encompass specific immunological principles. Corticosteroids and other immuno-suppressive reagents may be used to suppress the immune response in general. However, these agents are non-specific and produce undesirable toxic side-effects. They may also cause general bone marrow suppression and/or increased susceptibility to severe infection due to their non-specific effect on immune response.

There is, therefore, a real need for methods which can be used to effectively suppress undesired immune responses of the type indicated while obviating at least some of the disadvantages and problems encountered with prior treatments. The principal object of the invention is to provide such a method. Other objects, including the provision of new and improved vaccines, will also be hereinafter evident.

BROAD DESCRIPTION OF THE INVENTION

Broadly speaking, the method of the invention comprises administering to a subject suffering from an undesired immune response an effective amount of a non-immunogenic material of appropriate size and which carries a number of antigenic domains (i.e., "epitopes" or "haptens") which correspond to the antigen, e.g. the allergen or self-antigen which causes the allergy or autoimmune disease responsible for the undesired response. The haptens bind to cell antigen receptors specific to the indicated haptens and, provided the hapten number is sufficient and the carrier size is below an ascertainable threshold limit so as to avoid the formation of a stimulatory cluster of antigen receptors, as discussed below, the administered material serves to suppress the specific immune response.

Stated another way, the invention contemplates the therapeutic suppression of a specific undesired immune response by the administration of specific forms of antigen of controlled chemistry designed to competitively and non-productively bind to the antigen receptors, thereby preventing stimulatory antigen from causing the undesired response. The administered material operates by specifically suppressing the production of antibody to a particular allergen or self-antigen which is of concern, without compromising or damaging the general immune competence of the body. The method of the invention, therefore, deals only with a specific immune response and not with the immune response in general, According to the invention, the offending antigen, e.g. allergen or self-antigen, is identified so as to provide a molecular entity which contains a single or very small number of antigenic domains (epitopes or haptens). An appropriate number of these molecular entities containing the desired number of epitopes or haptens is then bonded by covalent linkage to a biologically inert substance, e.g. a polymer, or liposome, which functions as a carrier for the antigenic domains or epitopes. The carrier, with the thus-added epitopes or haptens is then administered to the subject in need of treatment to control the undesired immune response. In this connection, it will be appreciated that the carrier needs to be biologically inert only in the present context but may or may not be inert with respect to other biological functions.

The success of the invention is based on the dual findings that (a) there is a threshold number and spacing of haptens on a polymer carrier of appropriate size or the like which are essential to form a cluster of connected antigen receptors to stimulate antibody formation and (b) the presence of molecules containing a determined number of haptens on a polymer of sub-threshold size, not only will not stimulate antibody formation but more significantly, for present purposes, suppresses antibody formation by competing for the available antigen receptors. The present method utilizes this suppression finding (b) to control or eliminate the undesired immune response by suppressing antibody response.

The concept of there being a threshold limit as to the number and spacing of haptens to obtain an immunogenic response is disclosed in a 1976 paper we have co-authored with Vogelstein, entitled "Molecular Determinants of Immunogenicity: The Immunon Model of Immune Response," Proc. Nat'l. Acad. Sci. USA, Vol. 73, No. 10, pages 3671-3675, Oct., 1976. In that paper we have described some of our earlier work in which the immunological response in vivo to a series of size-fractionated linear polymers of acrylamide substituted with dinitrophenyl (Dnp) hapten, was measured in mice. The paper reports that a sharp threshold was observed in immunogenic response elicited by various polymer preparations. In particular, all polymers with less than 12 to 16 appropriately spaced hapten groups per molecule were non-immunogenic, while those polymers with greater than this number were fully immunogenic. The results indicate that the immunological response at its most elementary level is quantized, i.e., a minimum specific number of antigen receptors (maximally 12 to 16 for the work reported) must be aggregated as a spatially continuous cluster, an "immunon," before an immunogenic signal is delivered to the responding cell.

Our 1976 paper also discloses that the non-immunogenic polymers were suppressive of the action of immunogenic polymer towards triggering the de novo immune response in non-immunized animals. Apparently the suppressive effect of the non-immunogenic polymers is due to the fact that the haptens present compete for cell receptors and prevent the cluster (or immunon) formation needed to trigger the immune response. In other words, there is a competitive effect from the "sub-threshold" polymers, which bind receptors in clusters that are too small to act as immunons and consequently reduce the number of free receptors available to the immunogenic polymer molecules so that these latter molecules cannot find enough antigen receptors to form the clusters or immunons, or necessary number of these, to trigger the cell to antibody production. Regardless of the theory involved, however, it is evident that the non-immunogenic sub-threshold-sized polymers which carry less than the number of appropriately spaced haptens which are essential to stimulate the immune response, function to suppress the response. These non-immunogenic molecules are, therefore, suppressive of the stimulatory antigenic signal. Accordingly, injection of very small amounts of these non-immunogenic molecules results in a profound and long-lasting suppression of immune response.

While our 1976 paper discloses the suppressive action of the non-immunogenic polymer on the immunogenic effect of immunogenic Dnp-polyacrylamide, the paper does not disclose, and it is not obvious therefrom, that the suppressive effect of a non-immunogenic polymer carrying less than the threshold number of appropriately-spaced haptens can be used with advantage in the treatment of allergies or autoimmune diseases by suppressing or turning off the undesired immune response and resultant antibody formation. The 1976 paper also does not disclose the possibility of using proteins or liposomes as carriers for epitopes.

The suppressive effect of non-immunogenic polymers on the immunogenic response of immunogenic polymers is further described in three additional papers which we have recently co-authored entitled "Specific Cellular Stimulation in the Primary Immune Response: A Quantized Model," Proc. Nat'l. Acad. Sci. USA, Vol. 79, pp. 395-399, Jan. 1982; "Specific Cellular Stimulation in the Primary Immune Response: Experimental Test of a Quantized Model," Proc. Nat'l. Acad. Sci. USA, Vol. 79, pp. 884-888, Feb., 1982, "Studies on the Immunogenicity and Tolerogenicity of T-Independent Antigens", J. Immunol., Vol. 131, pp. 2196-2203, Nov., 1983. The contents of these 1982 and 1983 papers and our 1976 paper are incorporated herein by reference.

It will be appreciated that it is essential, for the practice of the invention, to first determine the antigen (e.g. allergen or self-antigen) which causes the undesired immune response. This means that the allergen or self-antigen, if not already known, must be identifiable. Once this is done, it is possible to construct the non-immunogenic molecule by known means to incorporate a selected number of haptens or epitopes corresponding to the allergen or self-antigen on an appropriate biologically inert, sub-threshold-sized synthetic or natural carrier material such as polyacrylamide, polyvinylpyrolidone, dextran, or like polymer, with less than the appropriately-sized haptens or epitopes essential to trigger the immune response. Alternatively, the carrier may be a relatively non-immunogenic self-protein such as an appropriately-sized aggregate of human serum albumin or gamma globulin or a liposome of appropriate composition and size (e.g. egg lecithin blended with an appropriate proportion of cholesterol and sonicated vigorously into the small size range of 250-400Å). As noted earlier, administration of the resulting molecule, e.g. by injection, results in binding of the haptens to the antigen receptor sites of the appropriate B-lymphocytes in a way which prevents or reduces the formation of the large receptor clusters essential to trigger the undesired immune response.

The invention is thought to be broadly applicable to the treatment of any allergy or autoimmune disease where the responsible allergen or self-antigen is known or identifiable. Obviously not all such allergens or self-antigens have as yet been identified or isolated. On the other hand, enough of these allergens or self-antigens have already been identified to enable the useful construction of molecules which are suppressive to the undesired immune response, according to the invention. It has been demonstrated that an ongoing immune response to the hapten, Dnp, can be suppressed by subsequent injections of a subimmunogenic Dnp-linear polyacrylamide preparation. The suppressive polymer used was of about 40,000 molecular weight. It was excreted relatively slowly from the body, and contained 11 Dnp groups per molecule. These groups were of sufficient number and density (about 100 Å apart) to non-productively bind cell-surface receptors and thus prevent formation of an immunogenic signal.

Correspondingly, it is believed that an ongoing immune response to an allergen or a self-antigen can be inhibited by the synthesis and injection of similar appropriate sub-immunogenic molecules as described below.

It will be appreciated that the number and spacing of the haptens on the carrier and the size of the carrier can be widely varied and will depend on other factors, e.g. the antigen involved and the carrier employed. However, the optimum number and spacing for a particular hapten or epitope as well as the carrier size can be determined without undue experimentation by simple tests on experimental animals such as mice, rats, rabbits or guinea pigs, using the selected polymer and hapten.

Since the desired suppressive effect appears to be based on competition for the cell receptors, it is usually preferred to use a number and spacing of the haptens which is relatively close to the immunogenic threshold limit rather than a substantially lower number. For example, if the immunogenic threshold limit for a particular antigen is determined to be about 20 haptens spaced 100-200 angstroms apart along a polymer chain of adequate size, a preferred non—immunogenic polymer could have 8-10 similarly spaced haptens on a smaller polymer. Less or more than this number of haptens could also be used, provided that the polymer carrier is less than the threshold size.

It will be evident from the foregoing that it is essential in each case to determine the threshold limit, in terms of the number and spacing of haptens and carrier size, necessary to obtain an immunogenic effect based on the particular carrier which is used and the specific antigen involved. This can be determined using the process described in our 1976 paper. Once the threshold number and spacing of haptens, and carrier size are determined, it is a straightforward matter to construct the corresponding non-immunogenic polymer molecule or the equivalent with the appropriate number and spacing of haptens or epitopes on a sub-threshold-sized carrier.

The ultimate aim in the construction of the non-immunogenic but suppressive molecule central to this invention involves covalent linkage of an appropriate number of haptens, epitopes or proteins containing epitopes, to a sub-threshold-sized carrier molecular scaffolding. A molecular entity will be thus created, capable of exhibiting on its exterior, a number of closely spaced ($\approx 100$ Å apart) haptenic or epitope groups capable of binding non-productively to B-cell surface immunoglobulin receptors.

The method for measuring effectiveness of suppression depends on the ability to measure decrease in circulating specific antibody concentration or (if possible, as in animal models), decrease in the number of antibody-secreting plasma cells. One of the advantages in the application of this invention is that it enables one to use extremely small (e.g., $\leq 0.5$ mgs/kg) quantities of administered suppressive molecules. This brings the dosage into pharmacologic range and greatly minimizes problems of toxicity.

The invention is illustrated by the suppression of an ongoing anti-Dnp antibody response by appropriate non-immunogenic Dnp polyacrylamide molecules, as previously described.

As other examples of the use of the invention, there may be mentioned the following:

(1) Suppression of Allergy to Pollen

Pollen may be fractionated to separate the major immunogenic protein materials in relatively pure form. This material may then be used to construct sub-immunogenic molecules by one or more of the following procedures:

(a) The protein may be covalently linked (e.g. by an amide bond between carboxyl and amino groups) to a carrier backbone polymer such as linear polyacrylamide or to a liposome.

(b) The epitope-containing pollen protein may be cross-linked to itself (e.g. using linking agents such as disuccinimidyl suberate) to form soluble "micro-grains" exhibiting a sub-immunogenic number of epitopes on their exterior surface. This would form a homogeneous "micro-grain" structure. Such a structure is possible only if the constituent proteins are soluble in physiological saline.

(c) If the epitope-containing pollen protein is insoluble, it may be solubilized with mild detergent (e.g. Triton-X-100), and cross-linked to a suitable soluble protein carrier (e.g. human serum albumin or human immunoglobulin). This would form heterogeneous "micro-grains".

(d) The specific antigenic epitope(s) of the pollen protein can be identified using standard molecular biological and/or protein chemistry techniques and artificial peptide (or non-peptide) analogues synthesized and covalently linked or conjugated to a carrier molecule of appropriate size.

(2) Suppression Of Auto-Immune Disease

This is dependent on the ability to identify the self-antigen being reacted against. For example, such self-antigens have been identified in myasthenia gravis and multiple sclerosis.

(a) Multiple Sclerosis

Auto-antibodies against myelin basic protein have been implicated in this disease. To construct suppressive molecules, one would synthesize sub-immunogenic molecules containing myelin basic protein as described above for pollen proteins.

(b) Myasthenia Gravis

Auto-antibodies against acetylcholine receptors of the neuro-muscular junction have been implicated in this disease. Again, one would proceed to construct suppressive molecules using one of the procedures described above, depending on which one is found to be most appropriate.

(3) Suppression of response to an antigen where those parts of the molecule acting as epitopes are chemically defined:

If it is known that only certain portions of the molecule stimulate antibody production (e.g. subsections of the myelin basic protein) it may be possible to chemically synthesize these polypeptide regions. One would then create sub-immunogenic (suppressive) molecules by covalently attaching these polypeptides to synthetic polymers or alternately by covalently attaching them to small cross-linked clusters of human serum albumin molecules or to liposomes analogous to the process described above (1d) for pollen.

DISCUSSION OF THE THEORY OF THE INVENTION

To further describe the invention there are given below the results obtained in using size-fractionated Dnp-polyacrylamide preparations in two kinds of experimental procedures: (i) measurement of the shape of the dose-response curve as a function of the dose of polymer as administered in vivo and in vitro and (ii) assessment Of the inhibitory effect on the response to immunogenic polymers caused by the presence of polymers that are not substituted with enough haptens to be immunogenic. These results are consistent with the general theory of primary immune responsiveness to T cell-independent immunogens which is based on the immunon model as described in our 1976 paper. This model assumes that (i) each cell capable of responding to a haptenated T cell-independent immunogen contains a large number of individual hapten receptor molecules on its membrane surface; (ii) close partial clustering of these receptors results from their sequential binding to appropriately spaced haptens on one immunogenic molecule; (iii) an immunon can be formed, but only very slowly, when the receptor cluster contains the critical number of linked receptors; (iv) the cell will receive a specific stimulus, when sufficient "immunons" have been formed, that initiates a complex and multistep process leading to cell division, cellular differentiation, and antibody production; and (v) the amount of the primary immune response that is induced in an animal not previously exposed to the hapten is directly related to the rate of immunon formation in the population of cells bearing receptors for the hapten.

The kinetic process of immunon formation is symbolized in FIG. 1 in which receptors on a cell surface are shown to be interacting with a molecule of immunogenic or stimulatory polymer S (FIG. 1a) or interacting with a molecule of non-immunogenic (or non-stimulatory) polymer N (FIG. 1b). Polymer N, which is not capable of causing a specific immune response at any dose because it is too small to have a sufficient number of appropriately-spaced hapten groups, has been found to inhibit strongly the immunogenic effects of polymer S. According to the model, the inhibition is caused by nonproductive competition for binding sites. The essential difference between the immunogenic molecule S and non-immunogenic molecule N is that the former can bind at least q cell receptor molecules, whereas the latter cannot (where q is the immunon number). The model assumes that once q cell receptors have been bound, the molecular cluster represented by $S_q$ can undergo a slow, irreversible structural transformation with rate constant k* to form immunons. Theoretical consideration of the differential equations describing the formation of immunons leads directly to a quantitative relationship expressing the immune response as a function of the concentration of immunogenic and nonimmunogenic molecules.

From this relationship it has been shown (see our Jan. 1982 paper) that if doses $D_S$ of immunogen and $D_N$ of nonimmunogen are injected into one animal and doses $D'_s$ and $D'_N$ are injected into a second animal, then the ratio r of immune response in the first animal relative to that in the second animal should be given by $$r = \frac{D_s}{D'_s} \left[ \frac{(q-1) D_s^{max} + D'_s + D'_N}{(q-1) D_s^{max} + D_s + D_N} \right]^q \quad [1]$$

where $D_s^{max}$ corresponds to the dose of immunogen giving maximum response in an animal—i.e., the peak of the dose—response curve. The peak of the curve corresponds to optimal occupancy of receptor groups by large molecular clusters. Addition of more immunogenic polymer causes a decrease in the average cluster size. Addition of nonimmunogenic polymer competes nonproductively for receptor sites. In either case, immunon formation is inhibited by nonproductive competitive inhibition. Thus, high-dose suppression by immunogenic polymer and suppression by nonimmunogenic polymer both operate by a common mechanism—competitive inhibition of immunon formation by nonproductive binding of specific receptors.

EXAMPLES

The invention is illustrated by the following examples:

EXAMPLE 1

Linear polyacrylamide substituted with Dnp hapten groups was prepared as described in our above-mentioned 1976 paper. Thus, linear polyacrylamide (Gelamide 250-American Cyanamid) with average molecular weight $5 \times 10^6$ was substituted with ethylene diamine in a manner analogous to that previously used for polyacrylamide beads (Inman et al, Biochemistry 8, 4074–4082 (1969)). Dnp derivatives were obtained by shaking the ethylene diamine substituted derivatives with excess fluorodinitrobenzene followed by extensive dialysis. The degree of substitution was determined from measurement of dry weight and optical absorbance at 360 nm. Preparations were labeled with $^{125}I$ substitution levels of approximately one per 2500 monomer units were obtained, corresponding to less than one $^{125}I$ per molecule labeled.

Dnp-substituted polymers were fractionated by gel filtration through 1 m long columns of Bio-Gel A-0.5 M agarose beads. These original fractions were further fractionated three more times to obtain relatively homogeneous preparations, as determined by sedimentation equilibrium measurement in the analytical ultracentrifuge.

Two Dnp-substituted polymer preparations were obtained having the following characteristics:

|  | Polymer B | Polymer D |
| --- | --- | --- |
| Molecular weight, $\times 10^{-5}$ | 0.8 | 1.8 |
| Acrylamide monomer subunits/molecule | 1050 | 2350 |
| Extended Length of polymer chain, A | 2600 | 6000 |
| Acrylamide monomer subunits/Dnp | 42 | 36 |
| Average distance between Dnp groups, A | 105 | 90 |
| Total Dnp groups/molecule | 25 | 66 |
| "Effective" Dnp groups/molecule | 8–12 | 22–33 |

Polymer B was not immunogenic while Polymer D was (see Table 1, 1976 paper noted above).

Polymers B and D were subjected to further column fractionation on Sepharose Cl-4B. Two preparations (N and S) were separated for further testing. Preparation N was a central subfraction of polymer B and preparation S was a central subfraction of polymer D. Measurement of partial specific volume (0.690 ml/g) and extrapolation of sedimentation equilibrium molecular weight to zero concentration gave values of 60,000 for N and 130,000 for S. These values together with dry weight and absorbance at 360 nm show N to contain 19 Dnp groups per molecule [7–9 "effective" or appropriately spaced] whereas S contains 43 Dnp groups per molecule (14–21 "effective"). Polymers N and 8 had almost identical "epitope densities" or degrees of substitution by hapten per molecular size unit.

Antibody Response. Polymer preparations were injected intraperitoneally in BALB/c mice in 0.5 ml of isotonic saline. After 6 days, blood was collected by bleeding from the tail, and the serum was stored at −30° C. until analysis. The concentration in serum of IgM antibody against Dnp was determined by a solid-phase binding assay. Surfaces covalently coated with Dnp-substituted gelatin served to bind the anti-Dnp mouse antibody, whose presence was then measured by a second incubation with $I^{125}$-labeled rabbit antibody against mouse IgM antibody.

In Vitro Culture and Assay. Mice were killed by cervical dislocation, and their spleens were minced in RPMI-1640 medium and pressed through a stainless steel mesh (60×60 mesh; 0,019-cm diameter). Cellular debris was allowed to settle, and the supernatant containing a dispersed-cell suspension was decanted, freed of erythrocytes by osmotic shock, and washed. Suspensions of nucleated spleen cells were then incubated with or without appropriate polymer in 60×15 mm tissue culture dishes containing $5 \times 10^7$ viable cells in a final volume of 7.5 ml. The incubation was carried out in 5% $CO_2$/95% water-saturated air at 37.0° C. The incubation medium consisted of RPMI 1640 medium enriched with 5% (vol/vol) heat-inactivated fetal calf serum, 2% (vol/vol) heat-inactivated horse serum, 4 mM glutamine, 100 units of penicillin and 100 $\mu$g of streptomycin per ml, and 50 $\mu$M 2-mercaptoethanol.

After 3 days of incubation, cells were harvested and washed. Assay for direct (IgM) anti-Dnp plaque-forming cells was performed.

Figure 2:
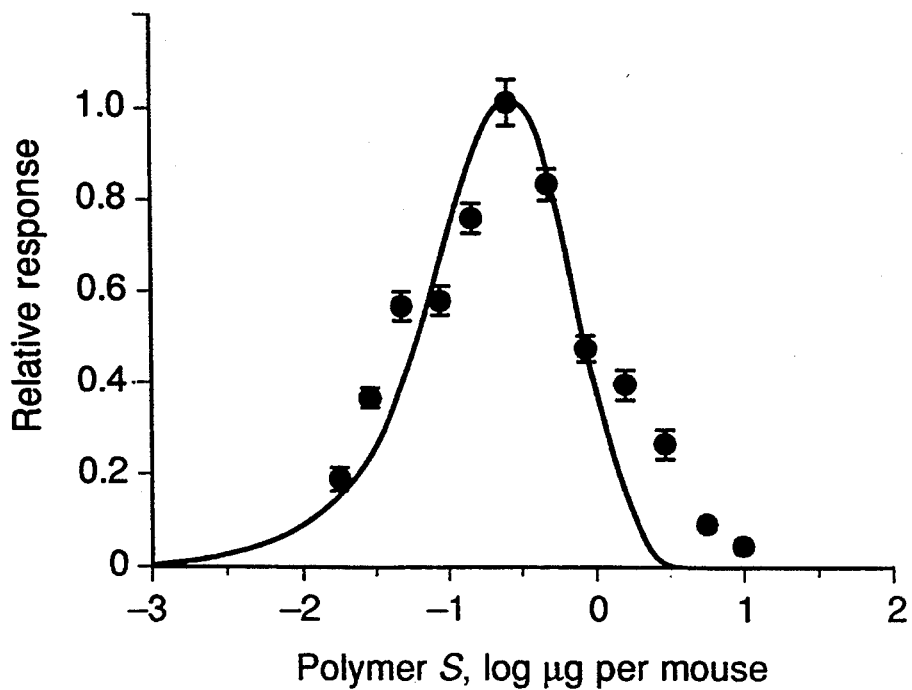

The immunological response in BALB/c mice 6 days after injection of various doses of immunogenic polymer preparation S, as measured by the concentration of serum IgM molecules reactive toward Dnp groups, is shown in FIG. 2. The mice in this experiment came in a single shipment of uniform age from the supplier and were divided into groups of 10. Members of each group were injected with the same dose, and all groups were handled as uniformly as possible. The solid curve in FIG. 2 is the theoretical response curve expected from Eq 1 as visually fitted to the experimentally determined points by adjustment of the numerical value of $D_S^{max}$ to 0.3 $\mu$g. In view of the simplicity of the assumptions involved in the derivation of Eq. 1 and the known variability of response of individual mice, the agreement between theory and experiment is surprisingly good. However, when the experiment was repeated by using different groups of mice supplied by the same breeder, the variability of biological responses in whole animals became more evident.

Figure 3:
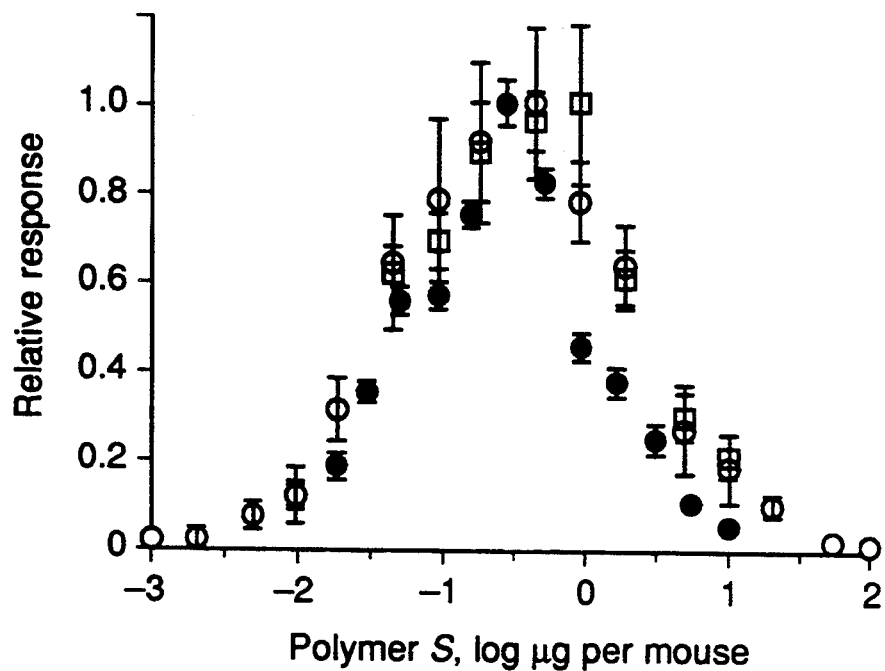

FIG. 3 compares the dose-response curves of three separate shipments of BALB/c mice and illustrates both group-dependent variability of response of individual mice at each dose and some change of shape of the dose-response curve from group to group. The variable immunological response given by different groups of mice is a well-known phenomenon, having been observed both in studies using whole animals and in those using cell cultures. It probably is dependent on factors in the previous history and handling of the animals, such as exposure to bacteria, viruses, and parasites, which might influence the "antigenic naivete" of the animals, as well as exposure to environmental shocks such as heat and cold during shipment.

By comparing the observed dose-response curves shown in FIGS. 2 and 3 with the theoretical curve shown in FIG. 2, it is clear that although the agreement between curves is good, the observed responses are quite variable from one batch of mice to another and, in general, show a wider dose-response curve than expected from the simple model that generated the curve shown in FIG. 2.

The wider experimental curve may be explained in the following way:

The theoretical curve in FIG. 2 is based on the assumption that all cells responding to the immunogen have receptor molecules with the same binding constant for Dnp groups. This assumption of complete homogeneity is unlikely to be true. If cells that bind immunogen and respond to it have protein receptors with differing binding constants for Dnp, then the predicted response should be the sum of a number of individual cellular response curves. Each curve would be like that in FIG. 2, but those with lower binding constants would be displaced to the right by an amount proportional to the ratios between their binding constants for Dnp. Inspection of FIGS. 2 and 3 from this point of view indicates that the observed width of the experimental dose-response curves may be understood as resulting from the summation of responses from individual populations of cells having receptors differing in binding constants by 1–1.5 log units—i.e., 10 to 30-fold. The dose-response measurements can be fit within experimental error by summing the theoretical responses of three or four such populations.

Figure 4:
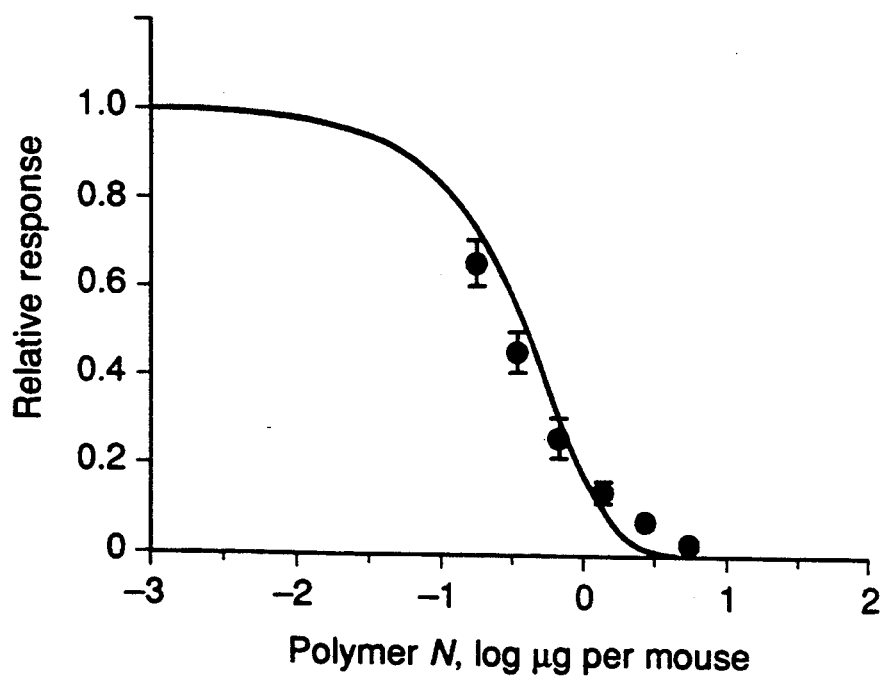

For a constant dose of immunogenic polymer, Eq. 1 also can be used to predict the extent of reduction of response that will be obtained with doses of increasing amounts of nonimmunogenic polymer N. Measurements of this type are shown in FIG. 4 for BALB/c mice. The solid line in FIG. 4 is not fitted to the data but is calculated directly from Eq. 1 by using the estimated value of the maximum-response dose $D_S^{max}$ of 0.5 $\mu$g per mouse obtained from FIG. 3. The agreement between the experimental points and the calculated theoretical curve in FIG. 4 is remarkable, if one considers the absence of arbitrarily adjusted parameters in this calculation.

Figure 5:
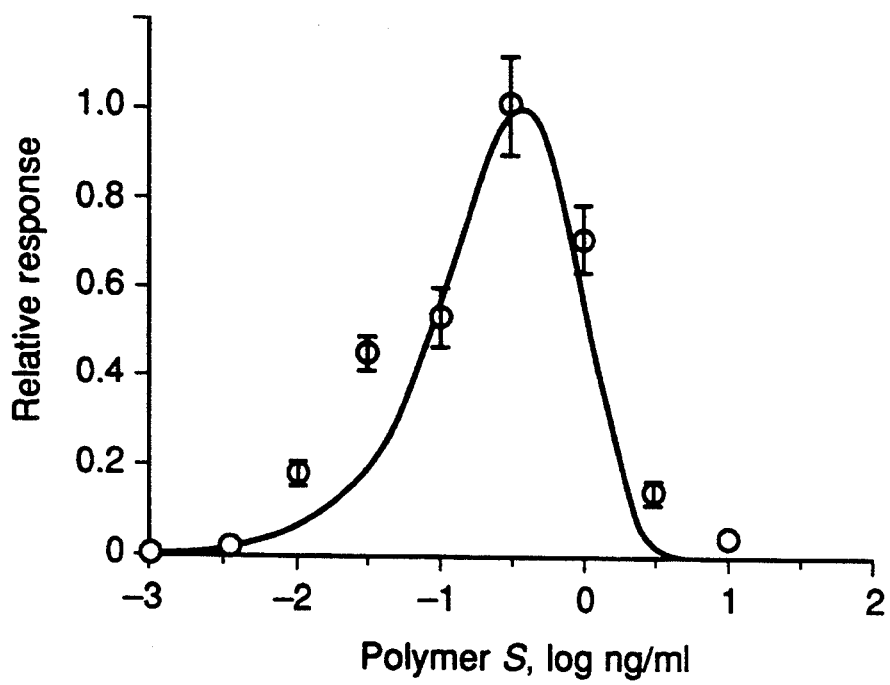

In addition to experiments in living animals shown in FIGS. 2, 3, and 4, dose-response curves were measured in vitro with isolated mouse spleen cells. FIG. 5 shows the results of such an in vitro experiment as compared with a visually fitted theoretical curve calculated from Eq. 1. This agreement between experiment and theory for the in vitro experiment with cultured spleen cells (FIG. 5) is approximately as good as it was for the in vivo experiment with whole mice (FIG. 2). In both cases, the measured response curve is somewhat broader than that predicted from a model based on a homogeneous hapten binding constant in the responding cells.

Figure 6:
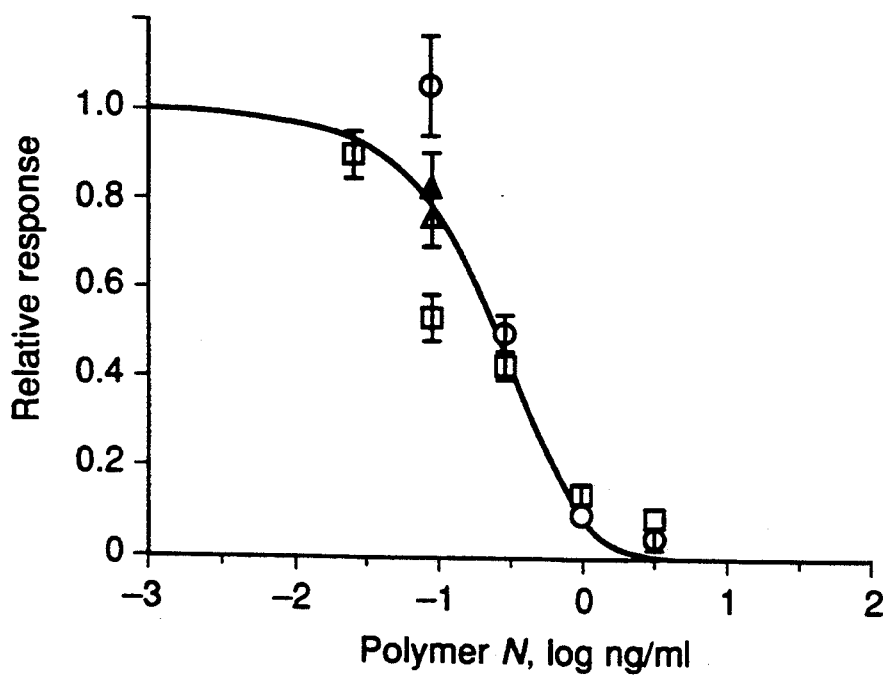

Of particular significance to the present invention are measurements of the inhibition of immune response in vitro with increasing amounts of nonimmunogenic polymer which are shown in FIG. 6. The solid line is not fitted to the data but is calculated directly from Eq. 1 by using the estimated value of the maximum-response dose, $D_S^{max}$, of 0.4 ng/ml from FIG. 5. There is substantial agreement between the experimental points and the calculated theoretical curve.

The blood volume and extracellular fluid volume of a mouse are each $\approx 1$ ml, so the optimal immunogenic polymer does in vivo is $\approx 1$ $\mu$g/ml. There is a large apparent discrepancy between this in vivo dose and that which is optimally immunogenic in vitro ($\approx 1$ ng/ml). The almost 1000-fold sensitivity difference is largely explained by rapid removal in vivo of polymer molecules by phagocytes located throughout the body. Studies with $^{125}$I-labeled preparations of the polymers as described in our 1976 paper showed that the bulk of the injected polymer is quickly removed from the circulation by Kupffer cells in the liver and phagocytic cells in other tissues. The resulting rapid fall in free polymer concentration, coupled with uncertainties concerning the rate of equilibration of polymer between different body fluid compartments makes difficult any quantitative comparison of relative optimum concentrations in vivo and in vitro. In spite of these difficulties, there remains the fact that the shapes of the dose-response and dose suppression curves measured in vivo are remarkable similar to those measured in vitro, implying strongly that the same limiting process is being probed in both cases. Furthermore, in both cases the measured responses as a function of dose are in excellent agreement with values obtainable from Eq. 1.

Although polymer N fails to stimulate at any dose, it inhibits polymer S at the same dose where polymer S is maximally stimulatory. This indicates a competition for surface receptors. Because both polymer preparations have almost identical "epitope densities" with a common carrier chemistry, this finding is in disagreement with theories that explain immunogenicity by invoking epitope density or polyclonal (i.e., nonspecific) activation by the "carrier."

DISCUSSION OF EXAMPLE 1

The data presented above indicates the following with regard to a specific T cell-independent stimulus: (i) a specific immunogenic signal is generated by the formation of immunons on the surface of a responsive cell, (ii) an immunon will form only after a sufficient number of surface receptors are clustered, and (iii) specific clustering of surface receptors occurs as a consequence of their being bound to linked haptens. This binding is specific for the hapten-receptor interaction and does not primarily depend on the "scaffolding" to which the haptens are attached. The underlying physical scaffold that links the haptens may be molecular in nature or may consist of a surface on which small hapten-containing structures are aggregated, as on the surface of an "antigen-presenting cell."

Nonspecific stimuli, such as mitogens, lectins, antibodies against cell surface proteins, and activating or inhibiting factors from other cells, may well influence the level of "irritability" of the responding cell, making it more or less likely to respond to a given amount of immunogenic signal or even to respond in the absence of specific signals. Factors from T cells and macrophages have previously been shown to enhance antibody responses nonspecifically. Mitogens are known to stimulate cells nonspecifically to secrete antibodies. Whether or not they do this directly or indirectly by a mechanism involving specific receptor aggregation is not known. However, in contrast to these nonspecific stimuli, the data herein indicates that specific stimulation occurs by means of the linkage of receptors by their specific binding sites into immunons; thus, cells displaying those receptors are stimulated to divide and differentiate into cells that will secrete specific antibodies.

It has been demonstrated above (and in our 1976, 1982 and 1983 papers) that molecules consisting of haptens linked to a flexible linear polymer are immunogenic only if they have a sufficient number of adequately spaced haptens. This finding with a T cell-independent antigen might at first seem contradictory to the fact that many protein molecules that are T cell-dependent antigens and which do not contain multiple identical antigenic sites are nevertheless antigenic. However, several studies have shown that the antigenicity of proteins in vivo depends on their state of aggregation. It is well-known that experimentally induced aggregation of protein molecules by physical methods (heat, adsorption to bentonite, emulsification with Freund's adjuvant) or by chemical methods (cross-linking with glutaraldehyde or alum) greatly enhances their antigenicity. Nonaggregated protein molecules centrifuged free of aggregates or collected from the sera of injected animals have been shown to be not immunogenic but tolerogenic, whereas aggregated material with presumed multiple antigenic sites produces an immune response. Therefore, it is possible that the minimum requirements for antigenicity as determined with simple T cell-independent polymer may have applicability to immune responses to a large variety of molecules, including T cell-dependent ones. It is in any case evident that the suppressive effect of the nonimmunogenic polymer, on the immunogenic polymer, as illustrated above, can be used to control undesired immune response. The amount of nonimmunogenic polymer so used will necessarily vary depending on the specific immune response which is involved, the polymer carrier, the effective number of epitopes involved, body weight and other factors. It is believed, however, that the administration of from 0.5 to 50 mg/kg body weight would be effective in controlling undesired immune response. The administration may be effected by, for example, injection using a sterile solution of the non-immunogenic polymer.

EXAMPLE 2—TREATMENT OF MULTIPLE SCLEROSIS

An autoimmune response to myelin basic protein believed to be a prime factor in the generation of the disease, multiple sclerosis. To generate a disease in mice comparable to the human disease, a number of mice can be stimulated to make antibody against myelin basic protein by injection with that protein in complete Freund's adjuvant. After a number of days, when antibodies have been formed and disease symptoms appear, a portion of the mice can also be injected with a nonimmunogenic polymer comprising a polyacrylamide carrier as used in Example 1 with a number (e.g. 6–10) of epitopes of myelin basic protein spaced along the polymer chain.

After an appropriate time, e.g., a few weeks, all of the test mice can then be sacrificed and examined for damage to nervous tissue and level of antibody. The amount of antibody and the extent of nervous tissue damage in the mice treated with nonimmunogenic polymer should be substantially less than that in the mice not so treated.

EXAMPLE 3—TREATMENT OF MYASTHENIA GRAVIS

Antibody mediated mechanisms are believed to be responsible for impairing neuromuscular transmission in the disease myasthenia gravis. The culpable antibody reacts against acetyl-choline receptors (AChR) at the neuro-muscular junction. Mice given an injection of purified acetyl-choline receptor in Freund's adjuvant and pertussis as additional adjuvant develop muscular weakness and fatigability characteristic of myasthenia gravis. Mouse acetyl-choline receptor can be purified from mouse muscle by the use of affinity chromatography columns containing $\alpha$-bungerotoxin. Once the experimental disease has been developed in mice, a portion of them can be "treated" by injection of a nonimmunogenic polymer comprising a polyacrylamide polymer of appropriate size substituted with 6–10 AChR, or effective portions thereof, per molecule. The "cure" of test mice can be followed by measurement of decrease of level of high affinity AChR antibody in the serum of treated mice as compared with level and affinity of AChR antibody in control (or untreated) mice.

In lieu of the polyacrylamide carrier, an appropriately sized liposome (e.g. 300A) could be used to carry the indicated 6-10 AChR, or effective portions thereof, on its exterior surface.

EXAMPLE 4—TREATMENT OF AUTOIMMUNE THYRODITIS

This disease, characterized by a lymphocytic infiltration of the thyroid and interference with normal thyroid function, is believed to be caused by an autoimmune mechanism whereby antibodies to thyroglobulin are formed.

The disease can be simulated in mice by injection of thyroglobulin in complete Freund's adjuvant. Within a number of days, the thyroid can be seen to be inflamed and infiltrated with lymphocytes; the severity of the disease is proportional to this infiltration.

The proposed "cure" will be elicited by injection of thyroglobulin oligomers. These can be produced by appropriate cross-linking of tetrameric thyroglobulin molecules into sub-immunogenic conjugates of approximately 2–4× the normal molecular weight. The cross-linking can be done as discussed above, using appropriate molecular ratios of di-succinimidyl suberate or equivalent cross-linking agents.

"Cured" animals will exhibit thyroid glands free of lymphocytic infiltrates and absence of circulating antibody molecules against thyroglobulin.

EXAMPLE 5—TREATMENT OF PENICILLIN HYPERSENSITIVITY

Penicillin hypersensitivity is believed to be caused by the combination of tissue proteins with the major penicillin breakdown product: benzylpenicilloyl (BPO). This combination can induce the formation of IgE antibodies against penicillin. These antibodies, in turn, are largely responsible for the induction of symptoms of hypersensitivity when penicillin is administered to sensitized individuals.

The proposed treatment involves chemical construction and injection of appropriate subimmunogenic polymers or lipsomes comprising BPO haptenic groups covalently linked to a carrier of polyacrylamide, human immunoglobulin, serum albumin or liposome. Cure can be evidenced by decrease in circulating serum anti-penicillin IgE levels as measured by skin tests (specifically, passive cutaneous anaphylaxis, PCA).

Models of disease induction and cure can be carried out in mice. Penicillin sensitivity can be induced by the administration of 1–10 micrograms of $BPO_3$ ovalbumin absorbed on 1 mg aluminum hydroxide injected intraperitoneally. After 12 days, serum IgE levels rise and remain high for several weeks, as measured by PCA in rats. Cure involves injection of the subimmunogenic polymers described above and will be exhibited by negative PCA results indicating lack of anti-BPO IgE antibodies.

It is contemplated that the invention can be used to treat a wide variety of autoimmune or allergic disorders in addition to those exemplified above, e.g. Graves' disease, insulin resistance, pemphigus or Goodpasture's syndrome.

It will be appreciated that various procedures, understandable to one in the art, may be used to add the desired hapten or epitope to the carrier. For example, epitopes may be covalently bonded to free amino groups of phosphotidyl ethanolamine present on the exterior surface of a liposome used as carrier. Similarly, Dnp groups can be added to a polymer carrier (e.g. polyacrylamide) in the manner described above in Example 1. A more detailed description of the procedure as used to make one gram of polymer substituted about 1/50 with Dnp is given below:

Mix 100 ml of ethylene diamine (EDA) with 50 ml of $H_2O$ and cool to room temperature. Add with rapid stirring 50 ml of a 2% solution of the polymer in water. Heat at 50° C. for 15 minutes, cool rapidly to room temperature and set to dialyze in ⅝ inch dialysis tubing, stirring in large chromatography jar, and changing water early morning and late afternoon for three days. The resulting solution should contain polymer substituted approximately 1/50 with EDA. The polymer is put into 250 ml screw top flasks (approx. 100 ml per flask) and solid $K_2HPO_4$ added to give 0.1M $K_2HPO$ (dissolve by shaking in rotary bath at 60° C.). Approx. 0.5 ml flourodinitrobenzene is added to each flask and the flasks shaken vigorously for 2-3 hours at 60° C. During this time the pH will drop slowly from ~9.0 to ~7.5 as the FDNB hydrolyzes and reacts. The solution is the allowed to cool to room temperature and stand overnight during which time a small amount of loose ppt. often forms. The supernatant is decanted into 15 ml centrifuge tubes and spun at top speed in the desk top centrifuge for 10 minutes to remove traces of ppt. The clear supernatant is dialyzed against distilled water (changing 2× daily) until all color stops dialyzing (usually 2 to 3 days).

| EDA Reaction Concectration | Temp of EDA Reaction, °C. | Time of EDA Reaction | Temp. of Dialysis | Substitution Level |
|---|---|---|---|---|
| 50% | Room Temp. | -0- | Coldroom 2–3° C. | 1/110 |
| 50% | 50° | 2 hours | Room Temp. | 1/15 |
| 50% | 50° | 30 min. | " | 1/30 |
| 50% | 50° | 15 min. | " | 1/50 |
| 50% | Room Temp. | 0 | " | 1/67 |
| 25% | " | 0 | " | 1/86 |
| 10% | " | 0 | " | 1/300 |
| 2.5% | " | 0 | " | 1/700 |

While the various drawings accompanying this specification have been referred to above, the following further comments as to the several figures may be useful:

FIG. 1 is a diagrammatic representation of the stepwise assembly of an immunon cluster, Φ. The solid rectangles represent mobile protein receptor molecules containing binding sites (cups). The curved solid lines represent flexible polyacrylamide molecules with attached Dnp groups shown as solid circles. Receptors are shown as reacting stepwise either with an immunogenic polymer, S, or with a nonimmunogenic polymer, N. Subscripts on S and N are used to designate polymer molecules bound to clusters of surface receptors of the specific number designated by the subscript. Polymer N cannot form immunons because it cannot simultaneously bind enough receptors (because $n<q$).

FIG. 2 sets out dose-response measurements showing the mean of the relative concentration, in serum from individual mice, of IgM antibody against Dnp at 6 days after injection of polymer S in amounts shown (10 BALB/c mice per point). Error bars indicate SEM when it is larger than the circle. The solid curve gives the theoretical response expected from Eq. 1 for a peak response occurring at a dose of 0.3 μg per mouse and an immunon size, q, of 10. The theoretical response is not sensitive to the value of q if q is greater than five. The peak of the response curve corresponds to approximately 30 μg of anti-Dnp IgM per ml of serum.

FIG. 3 shows dose-response measurements for different lots of BALB/c mice. Measurements were made on serum from individual mice. The mean of measurements on each group at each dose is shown, together with the SEM when it is larger than the symbol. Of the symbols used, the solid black dot represents ten mice per point (these points being the same as in FIG. 2); the open circle "o" represents five mice per point; and the symbol □ represents six mice per point.

FIG. 4 shows response-reduction measurements for increasing doses of nonimmunogenic polymer preparation N injected simultaneously with a constant dose of immunogenic polymer preparation S. Measurements were made on serum from individual mice. The mean of each group is shown together with the SEM when it is larger than the symbol. BALB/c mice, 10 mice per point; 0.31 μg of polymer S given to each mouse. The solid curve gives the theoretical response expected from Eq. 1 for an immunon size, q, of 10 and $D_s^{max}$ set equal to 0.5 μg per mouse as derived from FIG. 3. The theoretical response is quite insensitive to the value of q but is shifted left or right according to the value of $D_s^{max}$, with no change in shape.

FIG. 5 shows dose-response measurements regarding the relative number of direct anti-Dnp plaques produced from spleen cell cultures 3 days after the start of incubation in the presence of various concentrations of immunogenic polymer S. The data represent the mean of duplicate cultures with triplicate assays per culture; and SD is indicated when it is larger than the circle. The experimental peak response corresponds to ≈300 plaques per $10^6$ spleen cells with a blank (without polymer) of ≈20 plaques per $10^6$ spleen cells. The curve gives the theoretical response expected from Eq. 1 for a peak response occurring at a polymer concentration of 0.4 ng/ml and an immunon size, q, of 10.

FIG. 6 shows dose-reduction measurements for increasing doses of nonimmunogenic polymer preparation N incubated in spleen cell culture with a constant dose (0.3 ng/ml) of immunogenic polymer preparation S. Procedures and data treatment were as in FIG. 5. The different symbols show data obtained in separate experiments. The solid curve gives the theoretical response expected from Eq. 1 for an immunon size, q, of 10 and $D_s^{max}$ set equal to 0.4 ng/ml as derived from FIG. 5.

EXAMPLE 6—Vaccine Embodiment

The invention also includes, as an extension of the finding that nonimmunogenic polymer will suppress immunogenic polymer, the feature of improving the effectiveness or efficacy of vaccines by removing, or avoiding in the case of new vaccines, nonimmunogenic polymers. Many vaccines are derived from bacterial or virus products comprising mixtures of polymers of varying molecular weights. According to the invention, low molecular weight polymers can be sub-immunogenic and suppressive of the response to polymers of higher molecular weight. Accordingly, the present invention proposes to optimize the effectiveness of vaccines in one of the following ways:

(1) From a naturally occurring polymeric immunogen (e.g. pneumococcal polysaccharide type III), sub-immunogenic smaller polymers would be removed because they act to inhibit the immune response against larger polymers. Thus, for example, vaccines against bacterial pneumonia, according to the invention, would contain only immunogenic molecules of molecular weight no lower than 250,000.

(2) If naturally derived materials are not effective as vaccines (e.g. the polysaccharide of hemophilus influenza type B, or protein toxoids) the invention contemplates increasing effectiveness by polymerizing the material into molecules containing more than the threshold number of epitopes.

The polymerization process can be one of the following:

(a) self-polymerization by covalent bond formation;

(b) covalent bonding to a synthetic polymer carrier; or (c) covalent bonding to polymerized human protein such as serum albumin. In all of these embodiments or modifications, the essential feature is to provide a vaccine which contains immunogenic polymers but which has been so processed as to be free from suppressive polymers. This insures that the resulting vaccine will be as effective as possible by eliminating or avoiding the non-effective and suppressive polymeric materials. Fractionation of existing vaccines to remove low molecular weight non-immunogenic polymer can be accomplished using conventionally available techniques to up-grade existing vaccines or in making new ones.

Examination of three lots of pneumococcal polysaccharide Type III vaccine from commercial sources show that these contain polymers of varying molecular weight including a substantial amount of polymer in the order of 70,000 and lower. Removal of this lower molecular weight polymer so that the vaccine essentially contains only polymer of 250,000 molecular weight or above should improve the effectiveness of the vaccine. This is based on the concept that the lower molecular weight polymers are essentially nonimmunogenic but compete for receptor sites with the higher molecular weight immunogenic polymer and thus suppress the action of the latter. It is further noted in this regard that the use of too much immunogenic polymer can also have a suppressive effect due to competition for receptor sites which limits the desired immunon formation. Hence, it is important not only to avoid the presence of low molecular weight non-immunogenic polymers in vaccines but to determine the optimum amount for most effective use. This is especially true for young people.

As will be evident from the foregoing, the invention is not dependent on the nature of the hapten or carrier but on the molecular mass of the carrier and the hapten density, these physical characteristics (molecular mass, hapten density) determining whether or not the matter is immunogenic or non-immunogenic or suppressive. This is further illustrated by the following additional disclosure and exemplification of tests done using fluoresceinated carriers. In this further work, the molecular characteristics of five chemically different fluoresceinated (Fl)-polymers were systematically varied, and their ability to stimulate an anti-hapten immune response was measured. The polymers used as carriers were carefully size-fractionated and consisted of one natural polymer (dextran), one modified natural polymer (carboxymethyl cellulose), and three synthetic polymers (Ficoll, polyvinyl alcohol, and polyacrylamide).

The carriers varied in physical structure from the highly cross-linked Ficoll, to the somewhat branched dextran to the linear polyacrylamide, carboxymethyl cellulose and polyvinyl alcohol. Polymers were haptenated with Fl and size-fractionated so as to yield a panel of molecules with varying molecular mass, hapten valence and hapten density. Anti-Fl response to these haptenated polymers was measured in vivo after i.p. injection of the Fl-polymer in saline, and measured in vitro following culture with unfractionated spleen cells from naive mice.

In agreement with the foregoing exemplification involving Dnp-polyacrylamide, it was found that to be immunogenic, each of the Fl-polymers had to exceed a comparable threshold value of molecular mass and of hapten valence. Optimal immunogenicity occurred when the Fl-polymers had values of mass and hapten density lying within a predictable range. Immunogenicity decreased when these optimal parameters were substantially increased or decreased. Accordingly, it can be concluded that the immunogenicity of soluble haptenated polymers depends on predictable physical molecular characteristics, and is relatively independent of the chemical composition and conformation of the carrier polymer.

Polymer carriers selected to be haptenated were dextran (T2000, T500 and T70—Pharmacia); Ficoll (400 and 70—Pharmacia); carboxymethyl cellulose (medium viscosity—Sigma); polyvinyl alcohol (average molecular weight 115,000—Aldrich); and linear polyacrylamide (synthesized in aqueous solution from crystalline acrylamide).

The polymer carriers were conjugated with fluorescein by the following procedures: Reactive carboxyl groups were generated in polyacrylamide by partial hydrolysis in 0.05M $Na_2CO_3$—0.05M $NaHCO_3$, pH 10.1, at 20° C. (3). Amino groups were introduced into such deamidated polyacrylamide and also into dextran, Ficoll, polyvinyl alcohol and carboxymethyl cellulose according to the procedures disclosed by Inman, J. Immunol. 114:7044. Subsequently, the amino groups on the polymers were conjugated to excess fluorescein isothiocyanate at pH 9.2 in 0.1M $Na_2B_4O_7$. The polymers were then dialyzed exhaustively against the buffer used for subsequent gel filtration (0.1M NaCl, 0.001M EDTA, 0.02% $NAN_3$, 0.01M $KPO_4$, pH 7.4).

Fl-polymers were then repeatedly fractionated over 95 cm columns of Sepharose CL-2B, CL-4B and/or CL-6B; center cuts were taken repeatedly to give preparations of relatively narrow molecular weight distributions. Fl content was determined by measuring optical density at 496 nm in 0.01M $Na_2B_4O_7$ using a molar extinction coefficient of 72,000 for Fl. This measurement together with polymer dry weight measurement permitted calculation of epitope density. Molecular mass was determined by sedimentation equilibrium analysis in the analytical ultracentrifuge as known in the art (Proc. Natl. Acad. Sci 73:3671 1976). Measurements were performed at several polymer concentrations by using the short column method, and molecular mass was obtained by extrapolation to zero polymer concentration. Polymers used in experiments were dialyzed against PBS and were sterilized by filtration with the use of 0.22-μm Nucleopore filters.

For in vitro studies, suspensions of $2 \times 10^7$ nucleated spleen cells from naive mice (CAF./J female mice, mostly 8-10 weeks old) were cultured in a final volume of 2 ml with or without appropriate polymer in 15 ml sterile polystyrene centrifuge tubes placed at an angle of 3 degrees from the horizontal. After 3 days of incubation, cells were harvested and washed. Assay for direct (IgM) anti-hapten plaque-forming cells (PFC) was performed using a modification of the procedure described in Trans. Rev. 18:130 (1974). All cultures were done in triplicate and PFC assays were performed on each culture in duplicate. Immune response was expressed as PFC per $10^6$ spleen cells. Responses of control cultures without added antigen were subtracted from those of experimental cultures. Typically, this control measured $5+/-2$ PFC per $10^6$ cells.

Indicator cells in the plaque assay were hapten substituted at low density in order to minimize assay response to low affinity (i.e., non-specific) antibody. Substituted indicator cells were prepared by mixing 1 ml of packed burro red blood cells (BRBC) with a solution of 1 mg of fluorescein isothiocyanate dissolved in 9 ml of borate buffered saline (BBS; 0.9% NaCl containing 10mM sodium borate, pH 9.2). The mixture was then stirred for 1 hour at room temperature in the dark. The cells were centrifugally washed first in BBS and then 3 or 4 times in PBS. They were stored in PBS containing 0.11% glycylglycine for no longer than one week. They were washed in PBS before use. Fl-substituted BRBC were found to be as effective as Fl-polymer substituted BRBC in detecting anti-Fl plaque forming spleen cells in this system. Trinitrophenyl (Tnp) substituted indicator cells were prepared as described in J. Immunol. 131:2196 (1983).

In vitro studies were conducted in parallel with whole animal measurements in order to rule out possible differences in immunogenic behavior due to differential body excretion rates or organ and tissue distribution. Conversely, confirmation of in vitro findings by in vivo results eliminated concern that in vitro findings merely reflected artifacts of cell culture. Culture of unfractionated spleen cells was the in vitro assay of choice in order to mimic as closely as possible the cellular milieu to which these molecules might be exposed in the living animal.

For in vivo antibody response, polymer preparations were injected into mice intraperitoneally in 0.5 ml isotonic saline. Adjuvants were not used in any antigen administration because they could change the physical state of the antigen in such a way as to make interpretation of actual molecular mass of the administered antigen impossible. After 4 days, mice were sacrificed and their spleens removed for PFC assay. Responses of control mice injected only with saline were subtracted from those of experimental mice. Typically, this control measured $10+/-5$ PFC per $10^6$ cells.

For the doses of Fl-polymers used to generate anti-hapten responses, no more than 1% of the observed anti-Fl response could be generated when unsubstituted carrier was used as immunogen. When tested for non-specific polyclonal antibody generation, unhaptenated carrier molecules were found to generate no plaques against unsubstituted burro red blood cells (BRBC) or against BRBC substituted with either pneumoccoccal polysaccharide type 3 or with dinitrophenyl groups (data not shown). These observations indicated that, in the doses used to generate anti-Fl responses, Fl-polymers did not significantly stimulate B cells having epitope specificity distinct from fluorescein.

The composition and characteristics of the haptenated polymers used herein are listed in the following Table 1:

TABLE 1

| Polymer | Polymer Carrier | Carrier Composition | Carrier Characteristic |
|---|---|---|---|
| Fl-PA | Polyacrylamide | Synthetic polyethylene polymer | Linear homopolymer, uncharged |
| Fl-Fic | Ficoll | Polysaccharide synthesized from sucrose | Three-dimensional & highly cross-linked |
| Fl-Dex | Dextran | Bacterial polysaccharide of glucose subunits | Predominantly linear, somewhat branched homopolymer |
| Fl-CMC | Carboxymethylcellulose | Carboxy-methylated plant polyglucose | Linear, negatively charged homopolymer |
| Fl-PVA | Polyvinyl alcohol | Synthetic polyethylene polymer | Linear uncharged hompolymer |

All of these polymer carriers were essentially uncharged with the exception of the CMC which is negatively charged. Haptenation with fluorescein resulted in substituted polymers which were hydrophilic and negatively charged.

Figure 7:
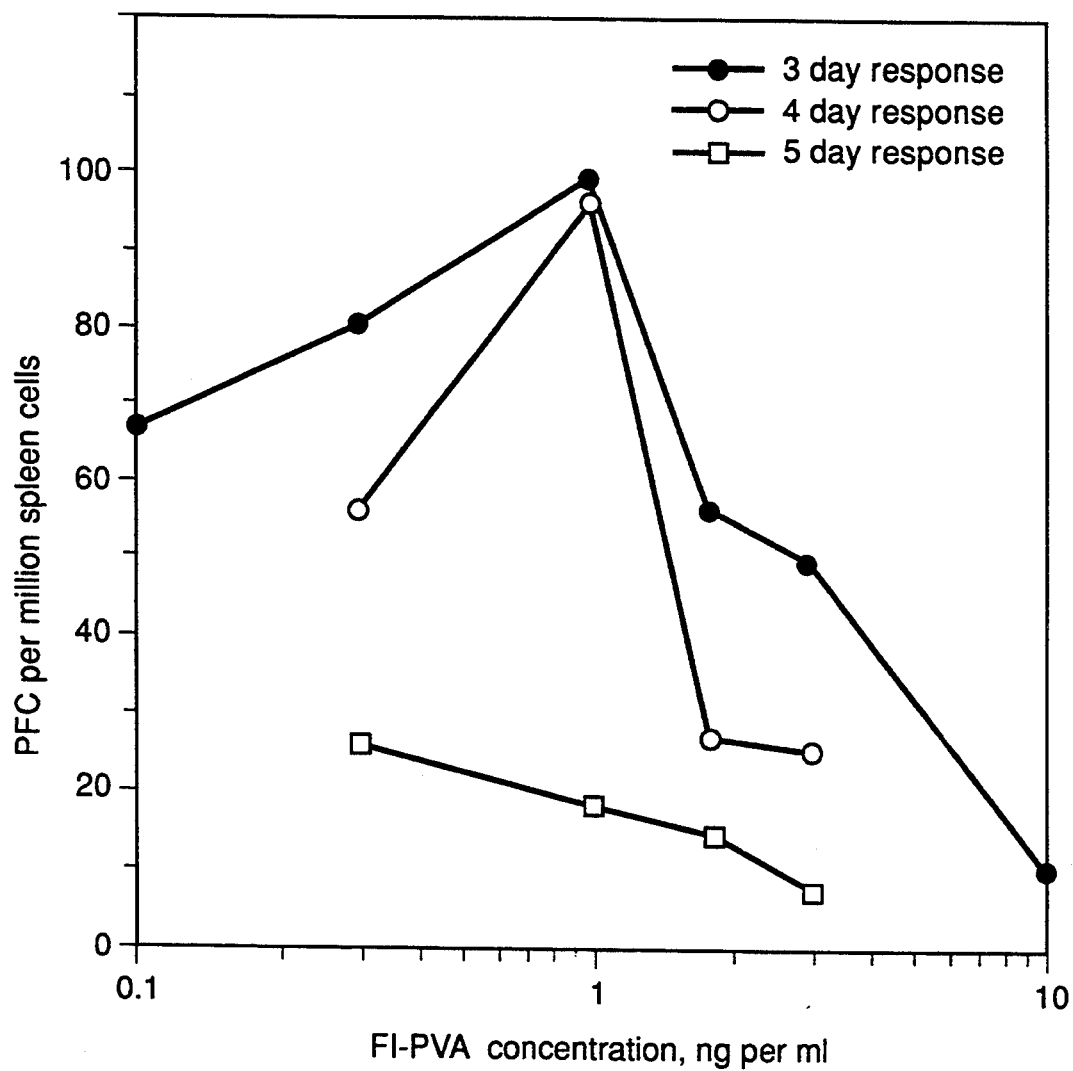

It was found that the kinetics of response to this series of Fl-polymers closely resembled those observed for Dnp-polyacrylamide. As an example, FIG. 7 shows dose-response curves of the primary in vitro anti-hapten response of naive spleen cells to Fl-PVA after various times of incubation. The peak in vitro response occurred after three days of incubation. The kinetics the primary in vivo anti-hapten response to the optical dose of the same polymer are pictured in FIG. 8. Spleen PFC peaked at about 4 days.

Figure 9:
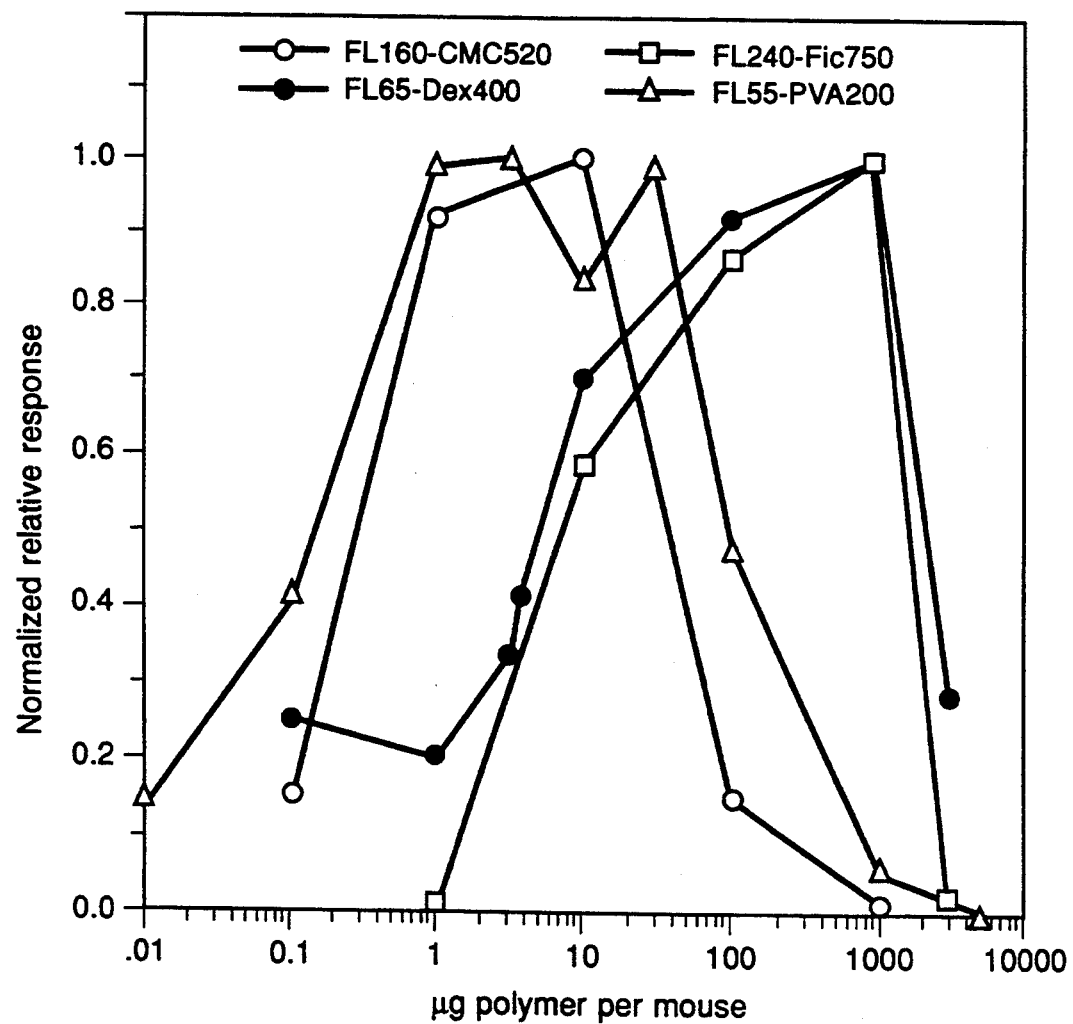

In vivo anti-hapten dose-response curves generated by four different fluoresceinated polymers, Fl-Dex, Fl-Fic, Fl-CMC and Fl-PVA, are shown in FIG. 9. In vivo dose response curves, shown in FIG. 10, include the curve generated by an additional polymer Fl-PA. These curves are representative of the responses generated by all the immunogenic polymers used in this study. Each dose-response curve is bell-shaped, initially increasing with the dose of antigen until a maximum is attained and then decreasing at higher doses of antigen.

Each of the size-fractionated polymers tested was consistent in behavior in vitro and in vivo being either immunogenic or nonimmunogenic in both situations. Table 2 lists a number of representative polymers with the results of assays for their stimulation of anti-hapten antibody responses.

TABLE 2

| Polymer | Density (mM Fl/gm polymer) | Immune Response (in vitro)[a] | Immune Response (in vivo)[b] |
|---|---|---|---|
| Fl$_{240}$Fic750 | 0.32 | + | + |
| Fl$_{90}$Fic750 | 0.12 | + | + |
| Fl$_{65}$Dex400 | 0.16 | + | + |
| Fl$_{60}$Dex170 | 0.35 | + | N.D.[c] |
| Fl$_{95}$PA300 | 0.32 | + | N.D. |
| Fl$_{230}$PA400 | 0.58 | + | N.D. |
| Fl$_{160}$CMC520 | 0.32 | + | + |
| Fl$_{26}$CMC110 | 0.24 | + | + |
| Fl$_{110}$PVA400 | 0.28 | + | N.D. |
| Fl$_{55}$PVA200 | 0.28 | + | + |
| Fl$_{14}$Fic40 | 0.35 | − | − |
| Fl$_6$Fic35 | 0.17 | − | − |
| Fl$_{14}$Dex40 | 0.35 | − | N.D. |
| Fl$_{47}$PA80 | 0.59 | − | N.D. |
| Fl$_6$CMC27 | 0.22 | − | − |
| Fl$_{14}$PVA50 | 0.28 | − | − |

[a]Determined by measuring direct anti-Fl PFC after 3 day culture of naive spleen cells with anitgen.
[b]Determined by measuring direct anti-Fl-PFC of spleen cells harvested 4 days after i.p. injection of antigen in saline without adjuvant.
[c]N.D. = not determined It is to be noted that the subscript number after the hapten abbreviation refers to the number of haptens per molecule (hapten valence), while the number after the carrier abbreviations refers to the molecular mass in kD. For example, Fl$_{65}$Dex400 refers to a molecule with 65 fluorescein groups on a dextran carrier, with a total molecular mass of 400,000 daltons.

Over a 4 log dose range, the group of polymers listed above the dotted line were immunogenic and the group below the dotted line were nonimmunogenic. Both groups included molecules with each of the five kinds of polymer carriers studied: Fl-Fic, Fl-Dex, Fl-PA, Fl-CMC and Fl-PVA. Thus all five Fl-polymers have the potential to be either immunogenic or nonimmunogenic, irrespective of the chemical composition of the polymeric carrier. Examination of the molecular characteristics of the polymers in Table 2 indicates that immunogenicity is directly related to the molecular mass and the hapten valence. All polymers above the dotted line, had a hapten valence greater than 20 and a molecular mass larger than 100,000 daltons and were immunogenic. Polymers below the dotted line had a molecular mass less than 100,000 daltons and were not immunogenic at any dose tested. The hapten densities in both groups had approximately the same range: between 0.12 and 0.59 millimoles of fluorescein per gram of polymer. Thus, hapten density by itself was not a predictor of the presence or absence of immunogenicity.

Table 3 shows the concentration of each polymer eliciting the maximum anti-Fl response as determined from the dose-response curves. The dose eliciting the maximum PFC response in vivo ranged from 3 to 300 ug/mouse. Molecules with a branched or partially branched carrier (Ficoll and dextran) appeared to require a higher dose to reach peak response than did molecules with linear carriers (polyvinyl alcohol, carboxymethyl cellulose, and polyacrylamide).

TABLE 3

| Polymer | Hapten Density (mM Fl/gm polymer) | Conc. Giving Max. Response (ug/mouse)[a] |
|---|---|---|
| Fl$_{65}$Pex400 | 0.16 | 300 |
| Fl$_{240}$Fic750 | 0.32 | 300 |
| Fl$_{90}$Fic750 | 0.12 | 100 |
| Fl$_{130}$Dex400 | 0.33 | 30 |
| Fl$_{160}$CMC520 | 0.31 | 10 |
| Fl$_{105}$CMC440 | 0.24 | 3 |
| Fl$_{55}$PVA200 | 0.28 | 3 |

[a]Maximal response concentrations were determined from dose-response curves obtained by PFC assay performed 4 days after i.p. injection of polymers in saline.

In contrast to the in vivo results, the peak in vitro anti-hapten responses for the majority of the polymers with different carriers occurred over a narrower concentration range, between 0.3 and 3 ng antigen per ml of culture fluid (Table 4). This may be due to the fact that culture eliminates some complexities of antigen distribution in the intact animal. Table 4 also shows that the molar concentrations eliciting the peak in vitro response for each immunogenic polymer occurred in the narrow range 1 to 8 pM for each polymer molecule, despite the differences in molecular mass, hapten valence and/or branching characteristic of the carrier. Although the data in Table 2 indicate that molecular mass and hapten valence are primary parameters in determining whether or not a molecule will be immunogenic, it can be seen that these parameters do not predict the magnitude of the response. All the polymers listed in Table 4 were immunogenic, yet the magnitude of the immune response varied from 15% to 90% of the response elicited by $Fl_{65}Dex400$, the most immunogenic polymer in this series. In this table of assorted immunogenic polymers, the molecular mass ranged from 300 to 2000 kD, and the hapten density ranged from 0.12 to 0.58 mmoles Fl per gm polymer.

TABLE 4

| Polymer | Hapten Density (mM Fl/gm polymer) | Conc. Giving Max Response (ng/ml) | (pM) | % Relative Response |
|---|---|---|---|---|
| $Fl_{65}Dex400$ | 0.16 | 3 | 8 | 100 |
| $Fl_{100}PVA400$ | 0.28 | 1 | 3 | 90 |
| $Fl_{90}Fic750$ | 0.12 | 3 | 4 | 85 |
| $Fl_{95}PA300$ | 0.32 | 0.3 | 1 | 60 |
| $Fl_{130}CMC520$ | 0.31 | 1 | 2 | 60 |
| $Fl_{240}Fic750$ | 0.32 | 1 | 1 | 60 |
| $Fl_{130}Dex390$ | 0.33 | 1 | 3 | 35 |
| $Fl_{230}PA400$ | 0.58 | 1 | 3 | 25 |
| $Fl_{640}Fic2000$ | 0.32 | 3 | 2 | 20 |
| $Fl_{170}CMC700$ | 0.24 | 1 | 1 | 15 |

[a]The dose of each polymer giving a maximal response was incubated with naive spleen cells for 3 days. The PFC response to the most immunogenic polymer, $Fl_{65}Dex400$, was assigned a value of 100%. PFC responses to the other polymers are relative to that response.

The effect of molecular mass and hapten density or the magnitude of the immune response for the Fl-polymers has also been studied.

Figure 11:
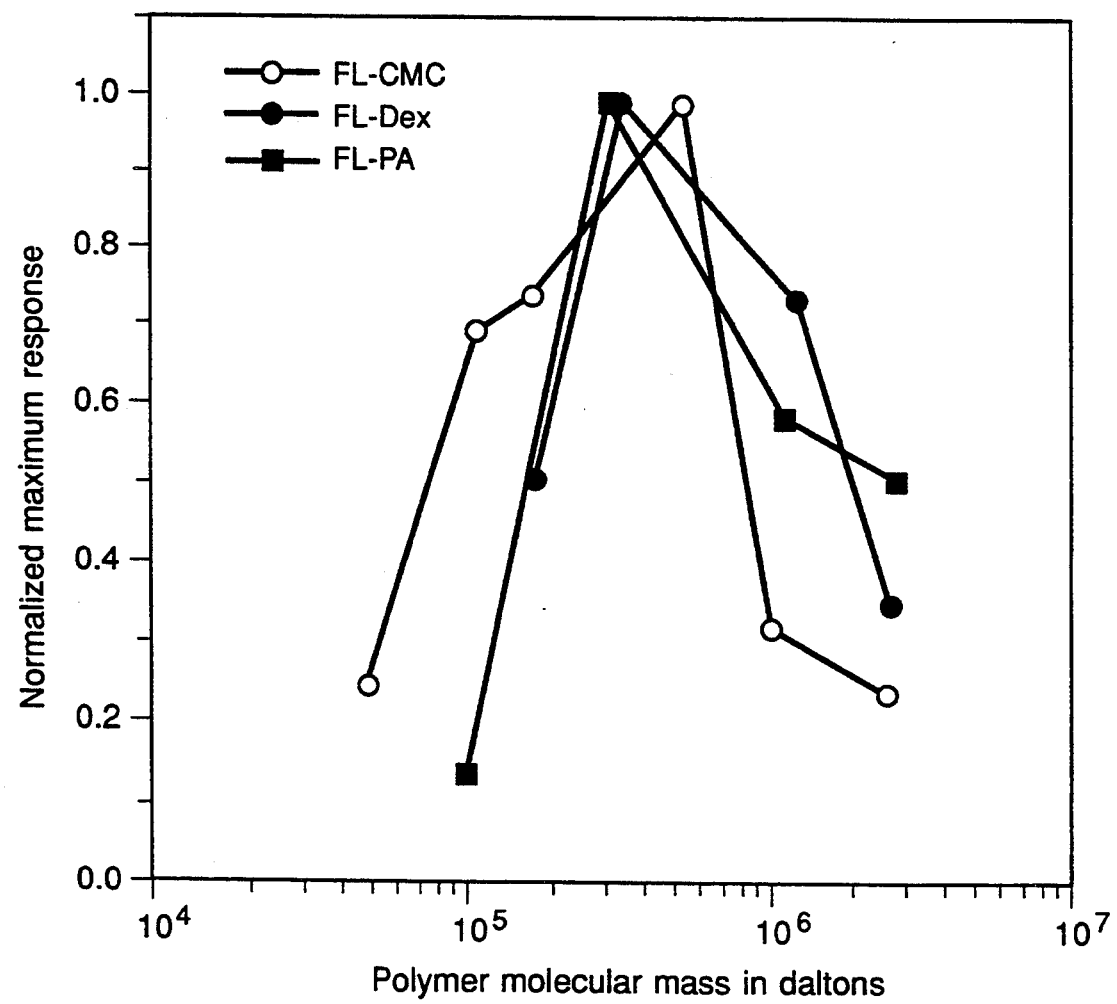

FIG. 11 illustrates the in vitro relative anti-hapten response normalized with respect to the optimal dose for each molecule in a series of Fl-polymers with different carriers. In each of the carrier groups (Dex, PA, and CMC), the molecules vary in molecular mass but have similar hapten densities, so that the average spacing between haptens in each carrier group is roughly the same, although the molecules vary substantially in size. It appears that for these polymers the molecular mass giving maximal immunogenicity is in the range of 200,000 to 500,000 daltons. For each of the carrier series, the response is significantly less for molecules which are smaller or larger than the 200 kD to 500 kD optimal mass range. This indicates that the optimal immunogenicity of haptenated polymers occurs over a restricted range of carrier size when hapten densities are similar.

The effect of hapten density on the magnitude of the response has also been studied. In this regard, the relative immunogenicity of four Fl-polymers with fixed molecular mass and varying hapten density mass examined at peak response. The polymers studied were in two groups with molecular masses of 400,000 and 750,000 daltons respectively. Table 5 lists the relative in vitro responses elicited by these polymers, compared to that of $Fl_{65}Dex400$, which was assigned a value of 100%. It is to be noted that in each group, the relative immunogenicity increased as hapten density decreased.

These observations indicate that there is a definable optimal hapten density when the molecular mass of a polymer of this type is kept constant.

TABLE 5

| Polymer | Hapten Density (mM Fl/gm polymer) | % Relative Response |
|---|---|---|
| $Fl_{65}Dex400$ | 0.16 | 100[a] |
| $Fl_{130}Dex390$ | 0.33 | 35 |
| $Fl_{90}Fic750$ | 0.12 | 85 |
| $Fl_{240}Fic750$ | 0.32 | 60 |

[a]The dose of each polymer giving a maximal response was incubated the naive spleen cells for 3 days. The PFC reponse to the most immunogenic polymer, $Fl_{65}Dex400$, was assigned a value of 100%. PFC response to the other polymers are relative to that response.

The foregoing shows that despite major differences both in carrier polymer and in the nature of the hapten group, the Fl-polymers give results which are similar to those attainable with Dmp-polyacrylamide. Thus, to be immunogenic, soluble Fl-polymers require a molecular mass exceeding about 100,000 daltons and a hapten valence greater than 20. Their immunogenicity depended on these identifiable molecular parameters, irrespective of the chemical composition of the carrier. Optimal immunogenicity was attained by Fl-polymers with a definable range of molecular mass and hapten density. Immunogenicity decreased when these optimal parameters were substantially increased or decreased.

EXAMPLE 8

The inhibiting properties of nonimmunogenic Fl-polymers are further illustrated by the following example.

Figure 12:
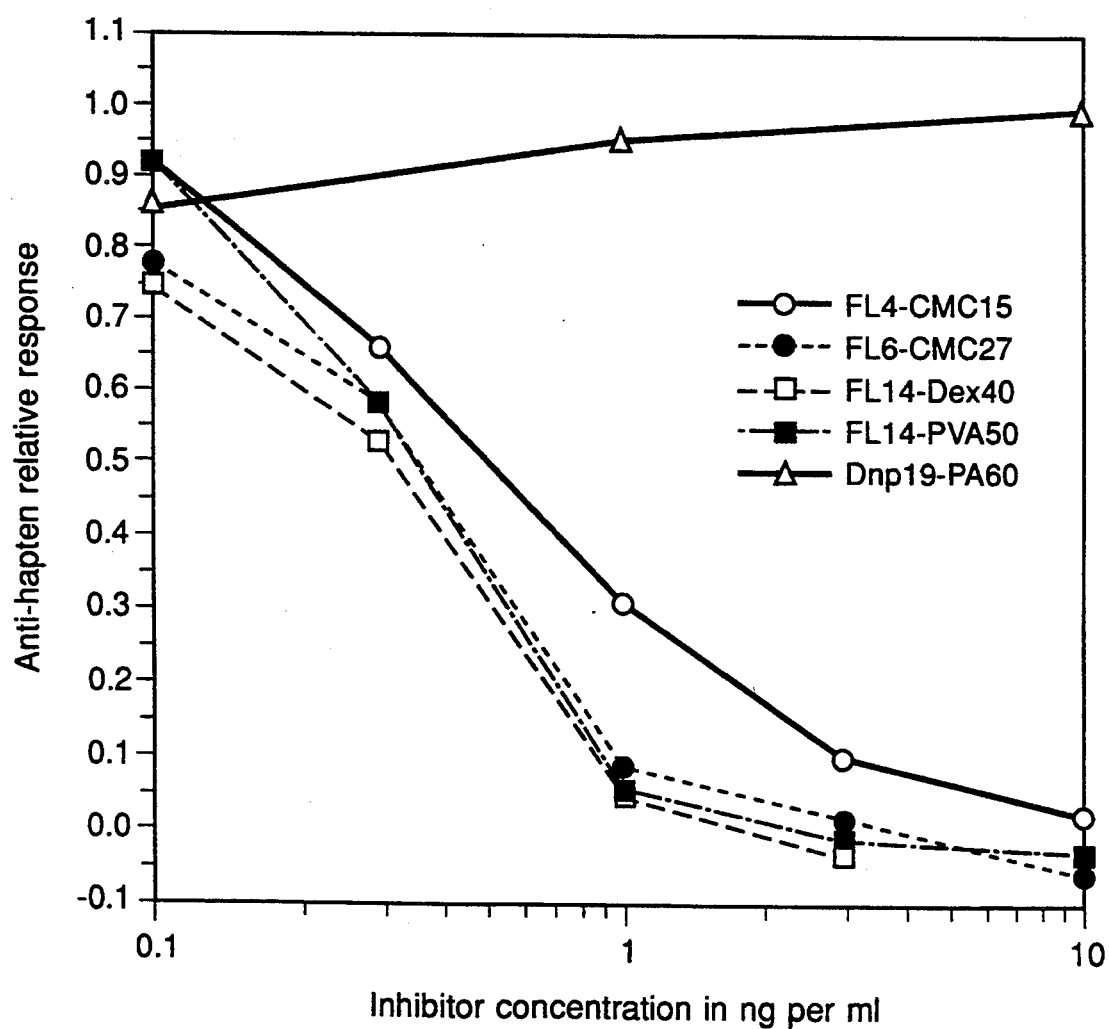

As shown above, soluble fluoresceinated polymers with molecular mass under 100,000 daltons and with hapten valence under 20 were unable to stimulate an anti-hapten response at any measured dose. However, this example shows that when mixed with optimal concentrations of stimulatory Fl-polymers and cultured with naive spleen cells in vitro, anti-hapten antibody production can be inhibited. FIG. 12 shows a representative example of such inhibition.

Naive spleen cells were cultured with a series of solutions formulated to contain increasing concentrations of the nonimmunogenic polymers together with a constant concentration of the immunogenic polymer $Fl_{90}Fic750$. As can be seen, the inhibitory ability of the nonimmunogenic polymers increases with increasing concentration until complete inhibition of the anti-Fl response to the immunogenic polymer is reached at inhibitor concentrations between approximately 1 and 10 ng per ml.

FIG. 12 demonstrates "cross-inhibition" whereby Fl on the backbone carriers, PVA, Dex, or CMC can inhibit the anti-Fl response stimulated by Fl-Fic. The data indicate that the inhibitory potentials of these nonimmunogenic Fl-polymers are largely independent of specific carrier chemistry. As a control, FIG. 12 shows that the irrelevant hapten, Dnp, on a PA carrier could not inhibit the anti-Fl response. Carrier-independent inhibition is further evidenced in Table 6, where the ability of four nonimmunogenic Fl-polymers to inhibit the immune response to four immunogenic polymers with different carrier backbones is shown.

TABLE 6

| Carrier Independent Inhibitory Ability of Fl-Polymers | | | | | |
|---|---|---|---|---|---|
| Inhibitory Polymer | Hapten Density (mM Fl/gm polymer) | Concentration[a] (ng/ml) for 50% Inhibition of Response to | | | |
| | | $Fl_{90}Fic750$ | $Fl_{65}Dex400$ | $Fl_{110}PVA400$ | $Fl_{105}CMC440$ |
| $Fl_{14}Fic40$ | 0.35 | 0.5 | 1 | 1 | 0.3 |
| $Fl_{14}Dex40$ | 0.35 | 0.35 | 2 | N.D.[b] | N.D.[b] |
| $Fl_{14}PVA50$ | 0.28 | 0.4 | 3 | 0.5 | N.D.[b] |
| $Fl_6CMC27$ | 0.22 | 0.4 | 2 | 1 | 1 |

[a]Concentration giving 50% inhibition was determined by measuring the decrease of direct anti-Fl PFC caused by adding the inhibitory polymer to a culture containing a constant amount of immunogenic polymer.
[b]N.D. = not determined The influence of hapten density and molecular mass individually on inhibitory ability was also measured. Table 7 compares the inhibitory abilities of pairs of Fl-polymers with similar molecular mass, but differing hapten densities. In each pair of molecules where the molecular mass was kept constant, the polymer with the higher hapten density was the better inhibitor, i.e., lower concentrations were required to cause a 50% inhibition of the response to $Fl_{90}Fic750$.

TABLE 7

| Effect of Hapten Density on Inhibitory Ability | | | |
|---|---|---|---|
| Inhibitory Polymer | Hapten Density (mM Fl/gm polymer) | Conc.[a] for 50% Inhib. of $Fl_{90}Fic750$ Response | |
| | | (ng/ml) | (pM) |
| $Fl_{240}Fic750$ | 0.32 | 5 | 7 |
| $Fl_{90}Fic750$ | 0.12 | 35 | 33 |
| $Fl_{230}Pa400$ | 0.58 | 2 | 5 |
| $Fl_{65}Dex400$ | 0.16 | 10 | 25 |

[a]Concentration giving 50% inhibition was determined by measuring the decrease of direct anti-Fl-PFC by adding the inhibitory polymer to a culture containing a constant amount (3 ng per ml) of $Fl_{90}Fic750$.

Table 8 compares the inhibitory abilities of two sets of polymers, one set with CMC as the carrier, and the other set with Ficoll as the carrier. The hapten densities in each set are similar, but the molecular weights differ. Included in the CMC carrier set are two nonimmunogenic polymers ($Fl_6CMC27$ and $Fl_4CMC15$); one nonimmunogenic polymer ($Fl_{14}Fic40$) is included in the Fic carrier set. In each set, regardless of immunogenic potential, the polymer with the higher molecular weight is the better inhibitor.

TABLE 8

| Effect of Molecular Mass on Inhibitory Ability | | |
|---|---|---|
| Inhibitory Polymer | Hapten Density (mM Fl/gm polymer) | Conc. (pM)[a] for 50% Inhib. of $Fl_{90}Fic750$ Response |
| $Fl_{105}CMC440$ | 0.24 | 2 |
| $Fl_{26}CMC110$ | 0.24 | 9 |
| $Fl_6CMC27$ | 0.22 | 15 |
| $Fl_4CMC15$ | 0.27 | 40 |
| $Fl_{640}Fic2000$ | 0.32 | 4 |
| $Fl_{240}Fic750$ | 0.32 | 6 |
| $Fl_{14}Fic40$ | 0.35 | 9 |

[a]Concentration giving 50% inhibition was determined by measuring the decrease of direct anti-Fl-PFC by adding the inhibitory polymer to a culture containing a constant amount (4 pM) of $Fl_{90}Fic750$.

While FIGS. 7-12 are discussed above, the following additional references thereto serve to more fully explain the data provided herein:

FIG. 7. In vitro response kinetics. The direct (IgM) anti-Fl response of naive spleen cells to increasing doses of $Fl_{110}PVA400$ was measured after 3,4, or 5 days of culture. All the S.D. were less than 10%.

Figure 8:
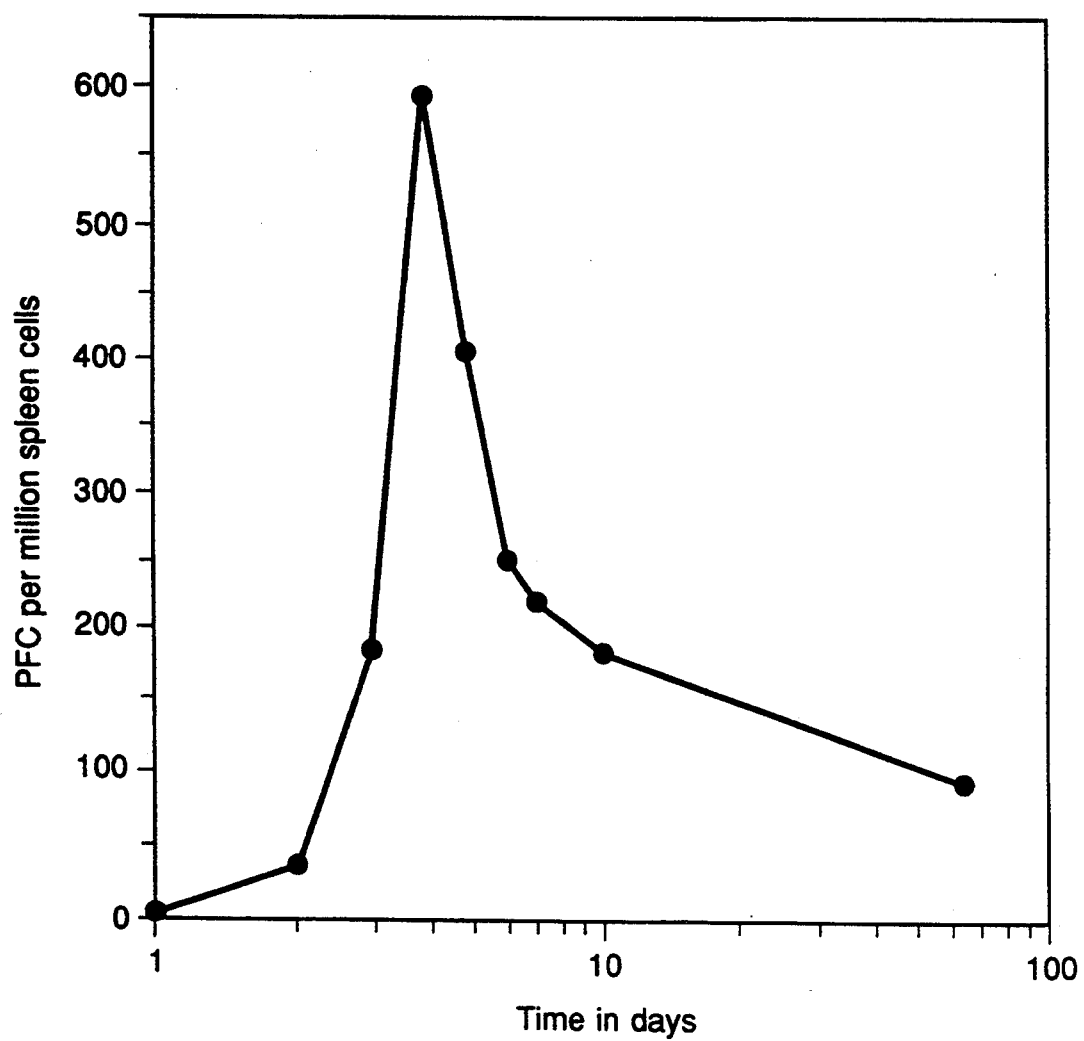

FIG. 8. In vivo response kinetics. An optimal dose of $Fl_{55}PVA200$ (10 μg/mouse) was injected i.p. in 0.5 ml saline, and direct (IgM) anti-Fl response was measured at times from 0 to 66 days. Each point represents 3 mice and is the mean of triplicate assays. The S.D. was less than 10%.

FIG. 9. In vivo normalized dose-response curves generated by four Fl-polymers with different carriers. Each point represents the mean of triplicate assays. Mice were injected with increasing doses of a Fl-polymer i.p. in saline (three mice/point), and PFC were measured after 4 days. Curves were normalized so that maximum response was assigned a value of 1, and other responses were expressed as fractions of the maximum response. The S.D. was less than 10%.

Figure 10:
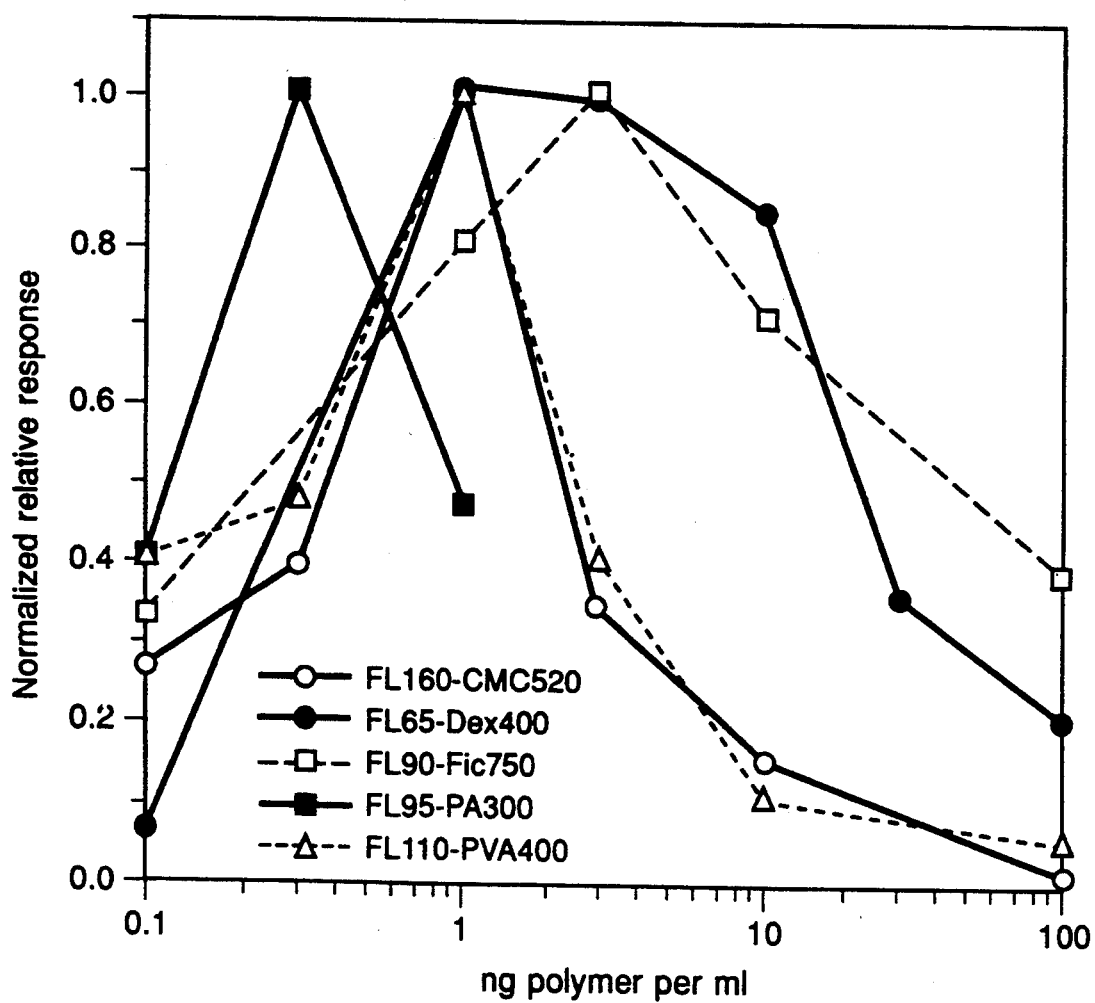

FIG. 10. In vitro normalized dose-response curves generated by five Fl-polymers with different carriers. Direct (IgM) anti-Fl PFC were measured after three days of culture of polymer with naive spleen cells. Curves were normalized so that maximum response was assigned a value of 1, and other responses were expressed as fractions of the maximum response.

FIG. 11. Effect of molecular mass of Fl-polymers on magnitude of anti-Fl response. The in vitro anti-Fl PFC response to an optimal dose of polymer was measured for three carrier groups of Fl-polymers with uniform hapten density and increasing molecular mass. The range of hapten densities (in mM Fl/gram of polymer) for each carrier group was as follows: Fl-PA (0.32–0.39), Fl-Dex (0.32–0.36), Fl-CMC (0.20–0.24). The peak response generated by each polymer of a given molecular mass was plotted as the fraction of the peak response generated by the most immunogenic polymer in that polymer carrier group. The Fl-Dex and Fl-Pa polymer preparations consisted of narrow distributions of molecular mass and were prepared by taking center cuts repeatedly in sequential gel filtration fractionations. The Fl-CMC preparations consisted of less sharply fractionated material from which center cuts were not taken. They therefore contained molecules with a broader range of molecular mass. Thus, the apparent immunogenicity of the 50 kD Fl-CMC can be explained since it contains a substantial proportion of molecules with molecular mass over 100 kD.

FIG. 12. Inhibition of the in vitro response to $Fl_{90}Fic750$ by non-stimulatory Fl-polymers. The IgM PFC response to $Fl_{90}Fic750$ alone was assigned a value of 1 and the response of cultures containing added amounts of nonimmunogenic polymers was expressed as the fractional relative response. The concentration of $Fl_{90}Fic750$ in each culture was kept constant at 3 ng per ml.

SUMMARY OF THE INVENTION

In summary, the invention contemplates, in one of its embodiments, administering, e.g. intravenously, a nonimmunogenic material which competes with immunogenic material and prevents the latter from triggering undesired antibody formation. It will be appreciated that the antibody production is eliminated or inhibited by suppressing the stimulation of the progenitor or precursor cells, rather than inhibiting the secretion of antibodies by plasma cells which are the progeny of the precursor cells. Plasma cells differentiate from stimulated precursor B-cells with receptors. It is the stimulation of the latter which is suppressed, according to one embodiment of the invention, by preventing the essential immunon formation through competition for cell receptors between immunogenic and nonimmunogenic material.

The further embodiment of the invention contemplates improving the effectiveness of vaccines by eliminating the nonimmunogenic material which is competitive with the effective immunogenic material.

Various modifications may be made in the invention as described above. Accordingly, the scope of the invention is defined by the following claims wherein:

What is claimed is:

1. A method of improving the effectiveness or efficacy of a polymeric vaccine by the elimination of nonimmunogenic polymers which compete with immunogenic polymers for B cell binding, comprising the steps of:

(a) selecting a polymeric vaccine consisting essentially of polymers containing multiple, repeating subunits of the same epitopes or haptens, (b) size fractionating said polymeric vaccine to remove polymers with molecular masses less than 250,000 Da, and (c) recovering the fraction of immunogenic polymers having molecular masses above 250,000 Da.

2. The method of claim 1, wherein the polymers are polysaccharides.

3. The method of claim 2, wherein the polymers are pneumococcal polysaccharide Type III.

4. A vaccine produced by the method of any one of claims 1, 2 or 3.

* * * * *